United States Patent
Ino et al.

(10) Patent No.: US 11,326,262 B2
(45) Date of Patent: May 10, 2022

(54) METHOD OF ELECTROCHEMICALLY PRODUCING HYDROGEL, METHOD OF PRODUCING HYDROGEL WITH PATTERN FORMED OF CELLS, HYDROGEL PRODUCTION APPARATUS, AND TRANSDUCER

(71) Applicants: TOHOKU UNIVERSITY, Miyagi (JP); JAPAN AVIATION ELECTRONICS INDUSTRY, LIMITED, Tokyo (JP)

(72) Inventors: Kosuke Ino, Miyagi (JP); Tomokazu Matsue, Miyagi (JP); Hitoshi Shiku, Miyagi (JP); Mayuko Terauchi, Miyagi (JP); Noriko Taira, Miyagi (JP); Ryota Kunikata, Tokyo (JP); Atsushi Suda, Tokyo (JP)

(73) Assignees: TOHOKU UNIVERSITY, Miyagi (JP); JAPAN AVIATION ELECTRONICS INDUSTRY, LIMITED, Tokyo (JP)

( * ) Notice: Subject to any disclaimer, the term of this patent is extended or adjusted under 35 U.S.C. 154(b) by 135 days.

(21) Appl. No.: 16/489,456

(22) PCT Filed: Jan. 24, 2018

(86) PCT No.: PCT/JP2018/002136
§ 371 (c)(1),
(2) Date: Aug. 28, 2019

(87) PCT Pub. No.: WO2018/168212
PCT Pub. Date: Sep. 20, 2018

(65) Prior Publication Data
US 2020/0040468 A1    Feb. 6, 2020

(30) Foreign Application Priority Data
Mar. 15, 2017    (JP) .............................. JP2017-049777

(51) Int. Cl.
*C25B 3/23*    (2021.01)
*C12M 1/12*    (2006.01)
(Continued)

(52) U.S. Cl.
CPC ................ *C25B 3/23* (2021.01); *B33Y 10/00* (2014.12); *C12M 25/14* (2013.01); *C25B 9/17* (2021.01);
(Continued)

(58) Field of Classification Search
None
See application file for complete search history.

(56) References Cited

U.S. PATENT DOCUMENTS

2005/0169962 A1* 8/2005 Bhatia ................ G01N 33/5044
424/423
2006/0102486 A1   5/2006 Bentlev et al.
(Continued)

FOREIGN PATENT DOCUMENTS

EP        2845612 A1    3/2015
JP    2008-204888 A     9/2008
(Continued)

OTHER PUBLICATIONS

European Office Action, European Patent Office, Application No. 18767765.3, dated May 13, 2020.
(Continued)

*Primary Examiner* — Louis J Rufo
(74) *Attorney, Agent, or Firm* — Greenblum & Bernstein, P.L.C.

(57) ABSTRACT

A hydrogel is formed by a reaction which is induced, in an electrolytic solution, by an electrode product electrochemically generated by electrodes installed in the electrolytic solution. An apparatus including an electrolytic tank with a bottom surface on which a two-dimensional array of work-
(Continued)

ing electrodes is provided and a counter electrode installed in the electrolytic tank is prepared. An electrolytic solution containing a dissolved substance that causes electrolytic deposition of a hydrogel is housed in the electrolytic tank. By applying a predetermined voltage to one or more selected working electrodes of the two-dimensional array, a hydrogel with a two-dimensional pattern corresponding to the arrangement of the selected working electrodes is formed.

19 Claims, 12 Drawing Sheets

(51) Int. Cl.
    *C25B 9/17*     (2021.01)
    *B33Y 10/00*     (2015.01)
    *C25D 13/04*     (2006.01)
    *C25D 9/02*     (2006.01)
    *B33Y 30/00*     (2015.01)
    *B33Y 80/00*     (2015.01)

(52) U.S. Cl.
    CPC .............. *C25D 9/02* (2013.01); *C25D 13/04* (2013.01); *B33Y 30/00* (2014.12); *B33Y 80/00* (2014.12)

(56) References Cited

U.S. PATENT DOCUMENTS

| | | |
|---|---|---|
| 2012/0103822 A1 | 5/2012 | Shi et al. |
| 2017/0051242 A1 | 2/2017 | Tokonami et al. |
| 2017/0281670 A1* | 10/2017 | Hoover .................. A61K 33/14 |

FOREIGN PATENT DOCUMENTS

| | | | |
|---|---|---|---|
| WO | 2015/166977 A1 | 11/2015 | |
| WO | WO-2016145182 A1 * | 9/2016 | ........... B29C 64/277 |

OTHER PUBLICATIONS

International Search Report issued in International Patent Application No. PCT/JP2018/002136, dated May 1, 2018.
Ozawa et al., "Three-dimensional cell culture using hydrogel microwell array fabricated by electrodeposition" the Electrochemical Society of Japan; pp. 2K03; Mar. 29, 2013.
Ozawa et al., "Electrodeposition of alginate gels for construction of vascular-like structures", Journal of Bioscience and Bioengineering, vol. 115, No. 4, pp. 459-461 (2013).
Ozawa et al., "Cell Sheet Fabrication Using RGD Peptide-Coupled Alginate Hydrogels Fabricated by an Electrodeposition Method", Chemistry Letters, Feb. 10, 2017, pp. 1-5.
Ozawa et al., "Alginate gel microwell arrays using electrodeposition for three-dimensional cell culture", Lab on a Chip, vol. 13, pp. 3128-3135 (2013).
Ozawa et al., "Electrochemical Hydrogel Lithography of Calcium-Alginate Hydrogels for Cell Culture", Materials, pp. 744-750 (2016).
Yi et al., "Signal-Directed Sequential Assembly of Biomolecules on Patterned Surfaces", Langmuir, pp. 2104-2107; Jan. 5, 2005.
Gray et al., "Electrodeposition of a Biopolymeric Hydrogel: Potential for One-Step Protein Electroaddressing", Biomacromolecules, pp. 1181-1189 (2012).
Notice of Reasons for Refusal (Office Action) in Japanese family member Patent Appl. No. 2017-049777, dated Apr. 23, 2018, and English translation thereof.
International Preliminary Report on Patentability (IPRP) for International Patent Application No. PCT/JP2018/002136, dated Sep. 17, 2019; including Written Opinion and English-language translation thereof.
Extended European Search Report issued in corresponding Application No. 21172384.6, dated Oct. 21, 2021.
Extended European Search Report issued with respect to Application No. 18767765.3, dated Aug. 14, 2020.

* cited by examiner

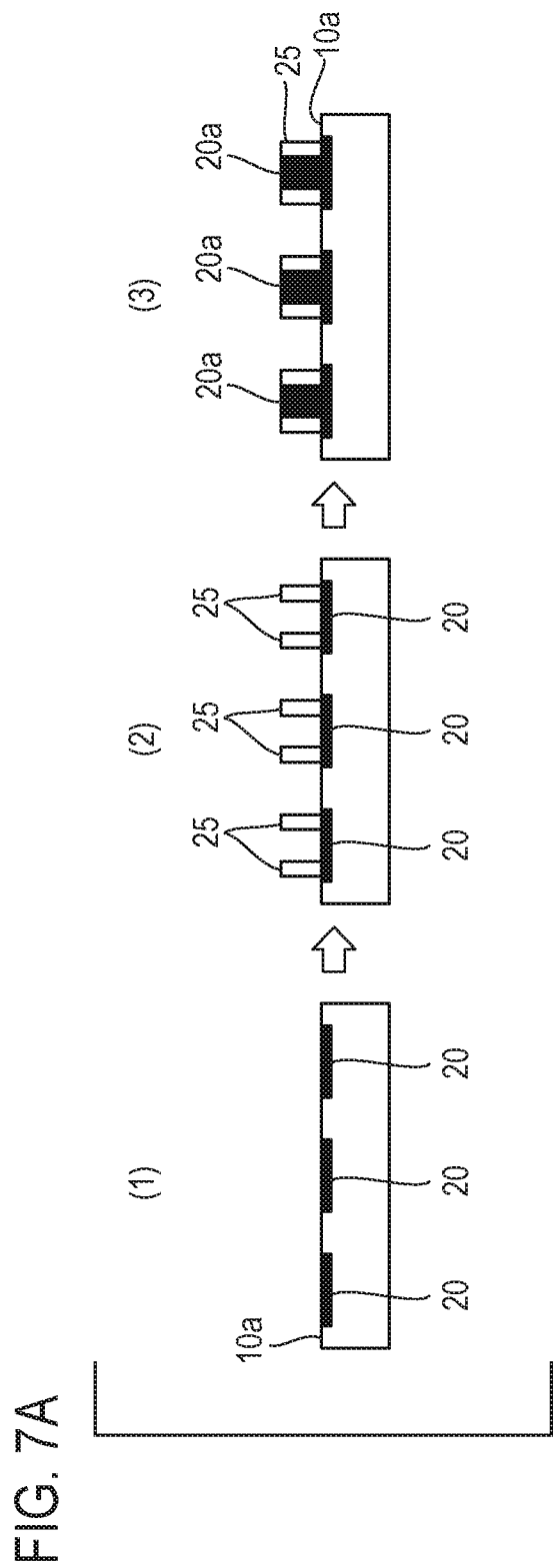

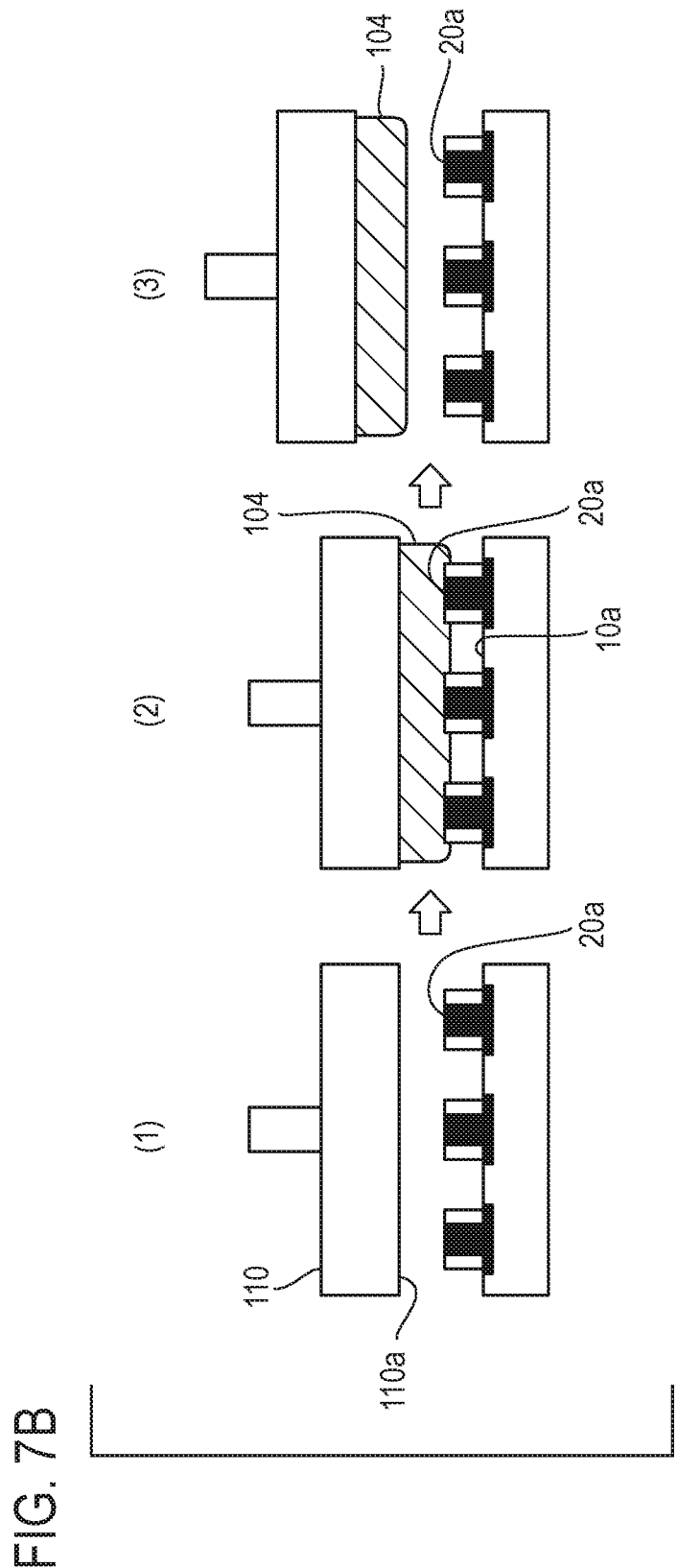

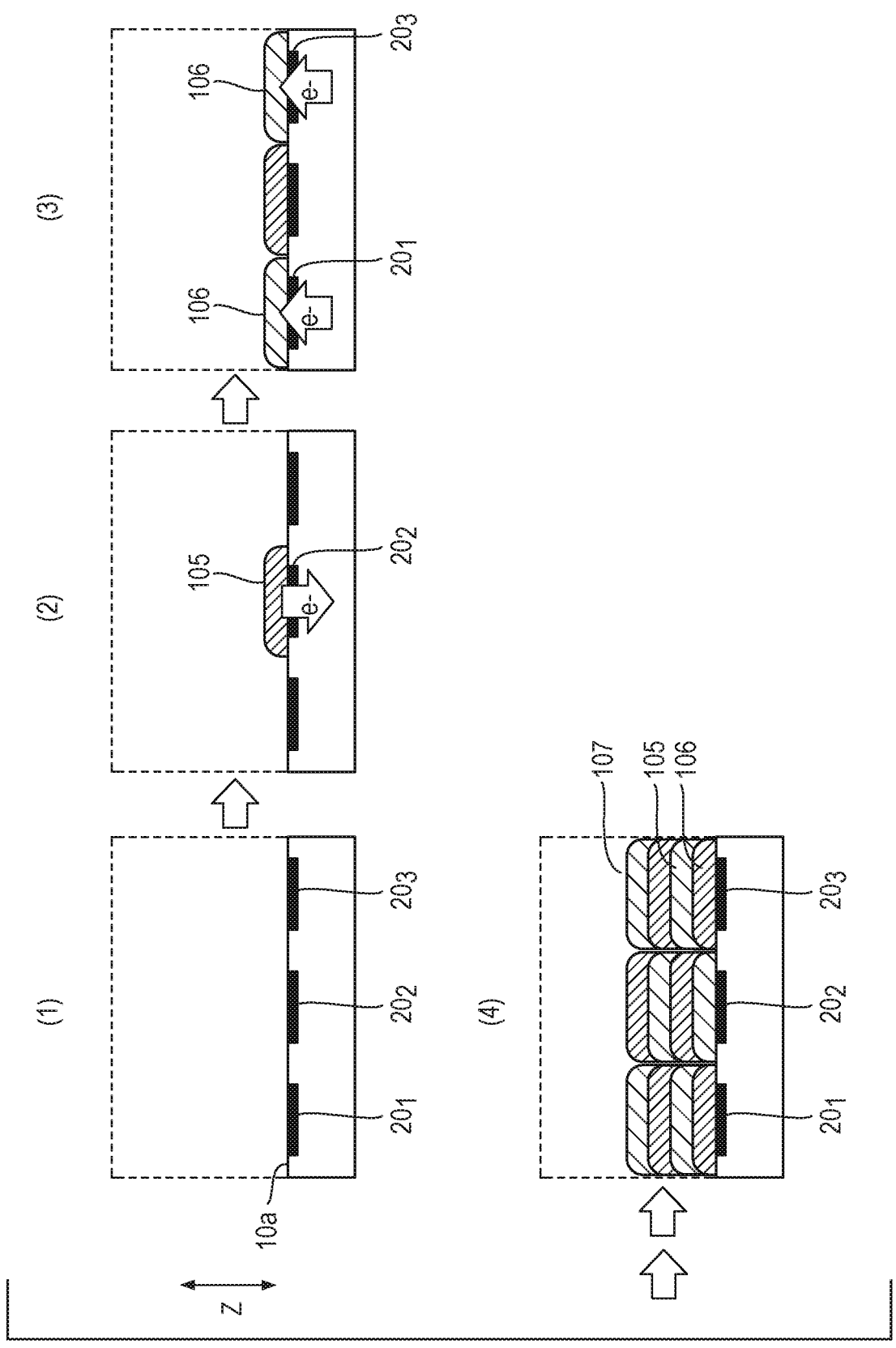

METHOD OF ELECTROCHEMICALLY PRODUCING HYDROGEL, METHOD OF PRODUCING HYDROGEL WITH PATTERN FORMED OF CELLS, HYDROGEL PRODUCTION APPARATUS, AND TRANSDUCER

TECHNICAL FIELD

The present invention relates to a method of electrochemically producing a hydrogel by using electrolytic deposition, a method of producing a hydrogel with a pattern formed of cells, a hydrogel production apparatus, and a transducer.

BACKGROUND ART

A hydrogel is used as a scaffold for cell culture, for example. A method of electrochemically producing a hydrogel by using electrolytic deposition is known.

Non-patent Literature 1 and Non-patent Literature 2 disclose methods of electrolytically depositing, on an indium tin oxide (ITO) electrode with a pattern, a hydrogel corresponding to the pattern. Non-patent Literature 3 and Non-patent Literature 4 disclose methods of electrolytically depositing a hydrogel by using a Pt wire electrode or by making a Pt wire electrode perform scanning in an electrolytic solution. Non-patent Literature 5 and Non-patent Literature 6 disclose techniques of electrolytically depositing a hydrogel or the like, by applying a voltage to one electrode selected from two electrodes or from among one-dimensional array of electrodes or, on the electrode.

PRIOR ART LITERATURE

Non-Patent Literature

Non-patent Literature 1: F. Ozawa et al., "Cell Sheet Fabrication Using RGD Peptide-Coupled Alginate Hydrogels Fabricated by an Electrodeposition Method", Chemistry Letters, Vol. 46, No. 4, pp 605-608, Advance Publication on the web Feb. 10, 2017. <http://www.journal.csj.jp/doi/pdf/10.1246/cl.170003>

Non-patent Literature 2: F. Ozawa et al., "Alginate gel microwell arrays using electrodepotion for three-dimensional cell culture", Lab on a Chip, 2013, 13(15), pp 3128-3135. <http://pubs.rsc.org/en/Content/ArticleLanding/2013/LC/c3lc50455g#!div Abstract>

Non-patent Literature 3: F. Ozawa et al., "Electrochemical Hydrogel Lithography of Calcium-Alginate Hydrogels for Cell Culture", Materials, 2016, 9(9), 744. <http://www.mdpi.com/1996-1944/9/9/744>

Non-patent Literature 4: F. Ozawa et al., "Electrodeposition of alginate gels for construction of vascular-like structures", Journal of Bioscience and Bioengineering, 2013, VOL 115, No. 4, pp 459-461. <http://www.sciencedirect.com/science/article/pii/S1389172312004409?via%3Dihub>

Non-patent Literature 5: K. M. Gray et al., "Electrodeposition of a Biopolymeric Hydrogel: Potential for One-Step Protein Electroaddressing", Biomacromolecules, 2012, 13(4), pp 1181-1189. <http://pubs.acs.org/doi/abs/10.1021/bm3001155>

Non-patent Literature 6: H. Yi et al., "Signal-Directed sequential Assembly of Biomolecules on Patterned surfaces", Langmuir, 2005, 21(6), pp 2104-2107. <http://pubs.acs.org/doi/abs/10.1021/1a047529k>

SUMMARY OF THE INVENTION

Problems to be Solved by the Invention

Non-patent Literatures 1 to 6 disclose the methods of electrolytically depositing a hydrogel. However, with the methods disclosed in Non-patent Literatures 1 and 2, only two-dimensional patterning can be performed. In addition, since the methods disclosed in Non-patent Literatures 1 and 2 make it necessary to produce an electrode for each pattern, the methods lack versatility. The methods disclosed in Non-patent Literatures 3 and 4 are methods by which a pattern is formed by using wire scanning, which is an extremely difficult and inefficient means, and can only form a limited and specific three-dimensional shape such as a tube. The techniques disclosed in Non-patent Literatures 5 and 6 are techniques of forming a hydrogel on one selected electrode and do not aim to perform shaping.

The present invention provides a technique of electrochemically producing a hydrogel, the technique that has a higher degree of flexibility in shaping, has greater versatility, and can form a hydrogel with a two-dimensional pattern or a three-dimensional pattern more efficiently than ever before.

Means to Solve the Problems

In one aspect, a method of electrochemically producing a hydrogel by using electrolytic deposition of a hydrogel, the method by which a hydrogel is formed by a reaction which is induced in an electrolytic solution by an electrode product electrochemically generated by electrodes installed in the electrolytic solution, includes a step of preparing an apparatus including an electrolytic tank with a bottom surface on which a two-dimensional array of working electrodes is provided and a counter electrode which is installed in the electrolytic tank, housing an electrolytic solution containing a dissolved substance, which causes electrolytic deposition of the hydrogel, in the electrolytic tank, and, by applying a predetermined voltage to one or more selected working electrodes of the two-dimensional array of the working electrodes, forming, on the bottom surface, the hydrogel with a two-dimensionally defined pattern corresponding to the arrangement of the selected working electrodes.

In an aspect, the method includes: a first step of forming a hydrogel with a two-dimensionally defined first pattern by applying a first voltage as the predetermined voltage to a first working electrode group as the one or more selected working electrodes; and a second step of forming a hydrogel with a two-dimensionally defined second pattern by applying a second voltage as the predetermined voltage to a second working electrode group as the one or more selected working electrodes. The second step is performed after the first step, and a hydrogel with a three-dimensionally defined pattern including at least two layers formed of the first pattern and the second pattern, which is located under the first pattern on the side thereof closer to the bottom surface, is formed.

In an aspect, in the method, at least one of the first step and the second step includes a first sub-step and a second sub-step, a corresponding one of the first working electrode group and the second working electrode group includes a first working electrode sub-group and a second working electrode sub-group, a corresponding one of the first voltage and the second voltage includes a first sub-voltage and a second sub-voltage, and a corresponding one of the first pattern and the second pattern includes a first sub-pattern and a second sub-pattern. The second working electrode sub-group consists of only the working electrode which does not belong to the first working electrode sub-group. A hydrogel with the first sub-pattern is formed by applying the first sub-voltage to the first working electrode sub-group and a hydrogel with the second sub-pattern is formed by applying the second sub-voltage to the second working electrode sub-group.

In an aspect, in the method, in the second sub-step, a hydrogel which dissolves under a predetermined condition is formed. In an aspect, the method further includes, at least after the first sub-step and the second sub-step, a sub-pattern removal step of selectively removing the hydrogel with the second sub-pattern by dissolving the hydrogel with the second sub-pattern by providing the hydrogel with the second sub-pattern with the predetermined condition.

In an aspect, in the method, a Z stage that has an adhesion surface facing the bottom surface parallel thereto and is displaceable in a Z direction perpendicular to the bottom surface is further prepared. By performing the first step with the Z stage being located in the electrolytic solution such that the adhesion surface is apart from the bottom surface by a first distance, a hydrogel with the first pattern whose upper surface, of two surfaces perpendicular to the Z direction, on the side farther apart from the bottom surface adheres to the adhesion surface is formed. After that, by displacing the Z stage with the adhesion surface, to which the upper surface of the first pattern adheres, in a direction in which the Z stage moves away from the bottom surface, a lower surface, of the two surfaces perpendicular to the Z direction, of the first pattern on the side closer to the bottom surface is moved away from the bottom surface by a second distance. By performing the second step with the first pattern being located in the electrolytic solution such that the lower surface is apart from the bottom surface by the second distance, a hydrogel with the second pattern connecting to the lower surface of the first pattern is formed.

In an aspect, in the method, the adhesion surface is subjected to treatment that makes the adhesion surface have an affinity for water.

In an aspect, in the method, all of the first working electrode groups are included in the second working electrode group and the three-dimensionally defined pattern has a structure in which the first pattern is supported from below by the second pattern.

In an aspect, in the method, all of the second working electrode groups are included in the first working electrode group and the three-dimensionally defined pattern has a structure in which the second pattern is supported from above, which is the side where the adhesion surface is located, by the first pattern so as to hang therefrom.

In an aspect, in the method, all of the working electrodes which compose the two-dimensional array protrude from the bottom surface and side faces of each protruding working electrode are surrounded with an insulating layer formed so as to protrude from the bottom surface along with the working electrode.

In an aspect, in the method, a part of the bottom surface other than front surfaces of the working electrodes is made water-repellent.

In an aspect, the method further includes a step of forming, on the bottom surface, a hydrogel with the two-dimensionally defined pattern corresponding to the arrangement of the selected working electrodes by applying the predetermined voltage to the selected working electrodes, and after that, in a state in which the formed hydrogel is in contact with the selected working electrodes, promoting separation of the hydrogel from the selected working electrodes by dissolving a contact part of the hydrogel with the selected working electrodes by applying a voltage for hydrogel separation, which is different from the predetermined voltage, to the selected working electrodes.

According to an aspect, in a method of producing a hydrogel patterned with cells, which is obtained by distributing predetermined cells over a hydrogel scaffold, by performing the method by using, as an electrolytic solution containing a dissolved substance which causes electrolytic deposition of the hydrogel, a suspension further containing the predetermined cells, a hydrogel with the distributed predetermined cells is formed on the bottom surface of the electrolytic tank.

In an aspect, in the, method the predetermined cells include one or more types of cells. In one aspect, the method, includes a step of performing the method by using, as the electrolytic solution, a suspension containing one type of cell of the predetermined cells along with a dissolved substance, which causes electrolytic deposition of the hydrogel, in any one of the first step and the second step.

In an aspect, the method includes a step of performing the method by using, as the electrolytic solution, a suspension containing the other type of cell, which is different from the one type of cell, of the predetermined cells along with a dissolved substance, which causes electrolytic deposition of the hydrogel, in the other of the first step and the second step.

In an aspect, in the method, the predetermined cells include one or more types of cells, and the method is performed by using, as the electrolytic solution, a suspension containing one type of cell of the predetermined cells along with a dissolved substance, which causes electrolytic deposition of the hydrogel, in any one of the first sub-step and the second sub-step.

In an aspect, the method is performed by using, as the electrolytic solution, a suspension containing the other type of cell, which is different from the one type of cell, of the predetermined cells along with a dissolved substance, which causes electrolytic deposition of the hydrogel, in the other of the first sub-step and the second sub-step.

In an aspect, the method includes, before a step of forming a hydrogel by applying the predetermined voltage to the selected working electrodes in a state in which the suspension is housed in the electrolytic tank, a dielectrophoresis step of densely distributing the predetermined cells on the selected working electrodes by dielectrophoresis by applying an alternating voltage of a predetermined frequency to the selected working electrodes.

In an aspect, in the dielectrophoresis step, an electrode with an electrode plane facing, parallel to the bottom surface, a region of the bottom surface in which the two-dimensional array of the working electrodes is provided is used.

In an aspect, in the dielectrophoresis step, an electrode which is provided on the bottom surface so as to be located around each of the two-dimensional array of the working electrodes is used.

In an aspect, the method includes, before a step of forming a hydrogel by applying the predetermined voltage to the selected working electrodes in a state in which the suspension is housed in the electrolytic tank, an electrophoresis step of densely distributing the predetermined cells on the selected working electrodes by electrophoresis by applying a predetermined direct voltage to the selected working electrodes.

According to an aspect, a hydrogel production apparatus that includes an electrolytic tank with a bottom surface on which a two-dimensional array of working electrodes is provided and a counter electrode, which is installed in the electrolytic tank, and can apply a predetermined voltage to one or more selected working electrodes of the two-dimensional array of the working electrodes includes a Z stage that has an adhesion surface facing the bottom surface parallel thereto and is displaceable in a Z direction perpendicular to the bottom surface.

In an aspect, in the hydrogel production apparatus, the adhesion surface is subjected to treatment that makes the adhesion surface have an affinity for water.

According to an aspect, in a hydrogel production apparatus that includes an electrolytic tank with a bottom surface on which a two-dimensional array of working electrodes is provided and a counter electrode, which is installed in the electrolytic tank, and can apply a predetermined voltage to one or more selected working electrodes of the two-dimensional array of the working electrodes, all of the working electrodes that make up the two-dimensional array protrude from the bottom surface and side faces of each protruding working electrode are surrounded with an insulating layer formed so as to protrude from the bottom surface along with the working electrode.

In an aspect, in the hydrogel production apparatus, all of the working electrodes that make up the two-dimensional array protrude from the bottom surface and side faces of each protruding working electrode are surrounded with an insulating layer formed so as to protrude from the bottom surface along with the working electrode.

In an aspect, in the hydrogel production apparatus, a part of the bottom surface other than front surfaces of the working electrodes is made water-repellent.

In an aspect, the hydrogel production apparatus includes an oscillator that can apply an alternating voltage of a predetermined frequency to the selected working electrodes.

In an aspect, the hydrogel production apparatus further includes an electrode for dielectrophoresis that is installed or can be installed in the electrolytic tank, and the electrode for dielectrophoresis is installed or can be installed in the electrolytic tank so that an electrode plane thereof faces, parallel to the bottom surface, a region of the bottom surface in which the two-dimensional array of the working electrodes is provided.

In an aspect, in the hydrogel production apparatus, the electrolytic tank further includes an electrode for dielectrophoresis and the electrode for dielectrophoresis is provided on the bottom surface so as to be located around each of the two-dimensional array of the working electrodes.

According to an aspect, in a transducer that includes an electrolytic tank, which can house an electrolytic solution and a hydrogel which is electrolytically deposited in the electrolytic solution, mounted on an LSI chip and is used for electrochemical production of a patterned hydrogel, in a shaping area defined on a bottom surface of the electrolytic tank, first electrodes which are provided in the LSI chip in a two-dimensional array arrangement are located. The transducer includes a Z stage with an adhesion surface, which can be installed in the electrolytic tank. The Z stage can be installed in the electrolytic tank so as be displaceable in a Z direction perpendicular to the bottom surface, in such a way that the adhesion surface faces the shaping area of the bottom surface parallel to the shaping area.

In an aspect, in the transducer that includes an electrolytic tank, the adhesion surface is subjected to treatment that makes the adhesion surface have an affinity for water.

According to an aspect, in a transducer that includes an electrolytic tank, which can house an electrolytic solution and a hydrogel which is electrolytically deposited in the electrolytic solution, mounted on an LSI chip and is used for electrochemical production of a patterned hydrogel, in a shaping area defined on a bottom surface of the electrolytic tank, first electrodes which are provided in the LSI chip in a two-dimensional array arrangement are located, and all of the first electrodes protrude from the bottom surface and side faces of each protruding first electrode are surrounded with an insulating layer formed so as to protrude from the bottom surface along with the first electrode.

In an aspect, in the transducer that includes an electrolytic tank, a part of the shaping area other than front surfaces of the first electrodes is made water-repellent.

In an aspect, in the transducer that includes an electrolytic tank, in the shaping area, a second electrode which is provided in the LSI chip so as to be located around each of the first electrodes is further located.

In an aspect, in the transducer that includes an electrolytic tank, the second electrode is formed over the entire surface of the shaping area without continuity between the first electrodes and the second electrode.

In an aspect, in the transducer that includes an electrolytic tank, a part of the shaping area other than front surfaces of the first electrodes and a front surface of the second electrode is made water-repellent.

In an aspect, the transducer that includes an electrolytic tank further includes a second electrode that is installed or can be installed in the electrolytic tank, and the second electrode is installed or can be installed in the electrolytic tank so that an electrode plane thereof faces the shaping area of the bottom surface parallel to the shaping area.

Effects of the Invention

According to the present invention, it is possible to achieve a higher degree of flexibility in shaping, achieve greater versatility, and form a hydrogel with a two-dimensional pattern or a three-dimensional pattern more efficiently than ever before.

BRIEF DESCRIPTION OF THE DRAWINGS

FIG. 7A is a diagram for explaining a method of forming the working electrode protruding from a bottom surface of an electrolytic tank.

FIG. 7B is a diagram for explaining the formation and separation of a hydrogel which are performed when the working electrode depicted in FIG. 7A is used.

FIG. 8 is a diagram for explaining the method of electrochemically producing a hydrogel (an embodiment).

DETAILED DESCRIPTION OF THE EMBODIMENTS

The principles and embodiments of a technique of electrochemically producing a hydrogel according to the present invention will be described with reference to the drawings.

First, the configuration of a hydrogel production apparatus will be described; then, the configuration of a transducer will be described.

First Embodiment

Figure 1:
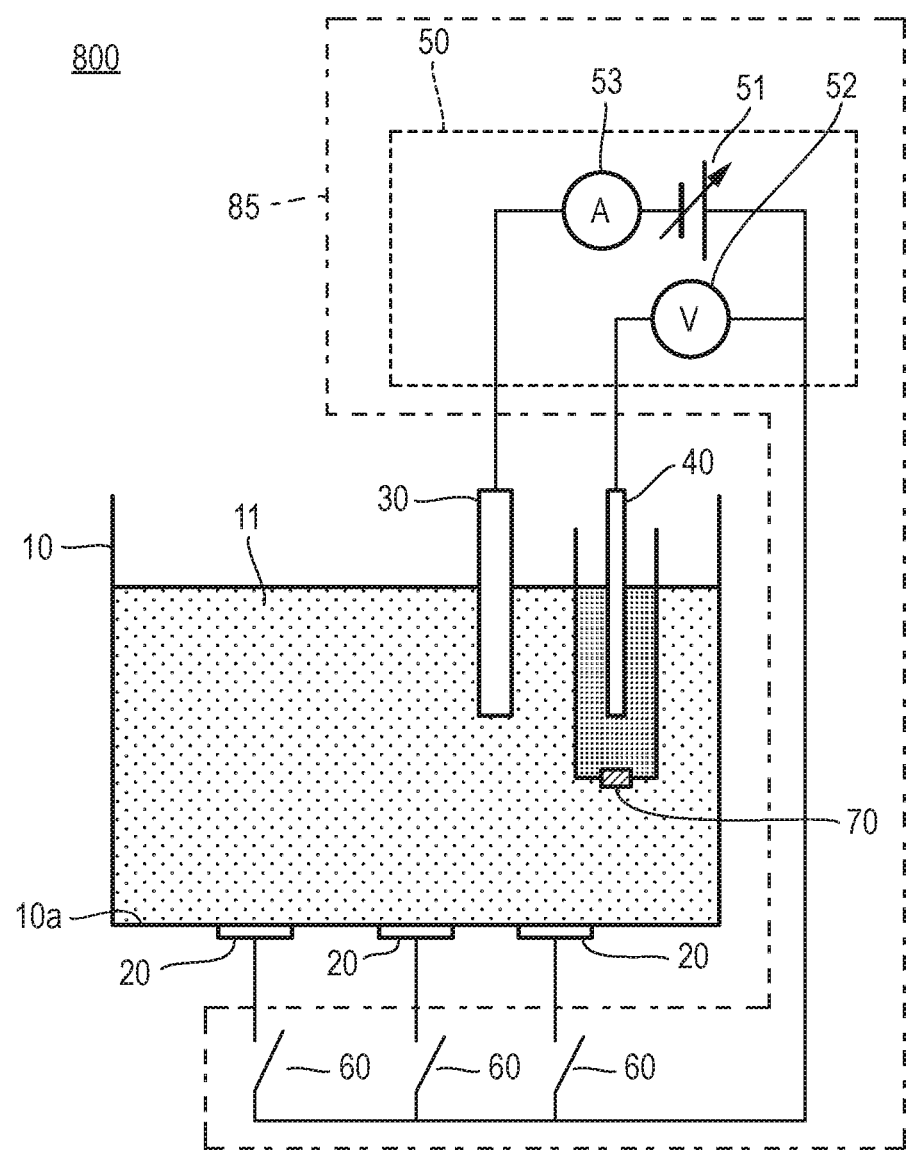
FIG. 1 is a diagram for explaining the configuration of a hydrogel production apparatus of an embodiment.

FIG. 1 is a schematic diagram explaining the configuration of the hydrogel production apparatus. A hydrogel production apparatus 800 illustrated as an example includes an electrolytic tank 10, working electrodes 20, one counter electrode 30, one reference electrode 40, and a controller 85. The electrolytic tank 10 can house an electrolytic solution 11 and a hydrogel which is electrolytically deposited in the electrolytic solution 11. The working electrodes 20, the counter electrode 30, and the reference electrode 40 are attached in the electrolytic tank 10 in this example. The working electrodes 20 are arranged on a bottom surface 10a of the electrolytic tank 10 with predetermined pitches in the form of a two-dimensional array (example: a two-dimensional grid-like arrangement; a detailed illustration thereof is omitted in FIG. 1). The controller 85 applies a voltage between the counter electrode 30 and one or more selected working electrodes 20 selected from among the working electrodes 20. The controller 85 includes a potentiostat 50 and switches 60. In FIG. 1, a reference numeral 70 denotes a salt bridge.

The counter electrode 30 and the reference electrode 40 are connected to the potentiostat 50. Each of the working electrodes 20 is connected to the potentiostat 50 via a corresponding one of the switches 60. The potentiostat 50 functions as a constant-voltage power supply device and is depicted as an equivalent circuit including a variable power source 51 and a voltmeter 52 (see FIG. 1). The application of a voltage between the counter electrode 30 and the working electrodes 20 is performed by the potentiostat 50.

The basic circuit configuration of the potentiostat 50 is the same as the basic circuit configuration of a potentiostat which is used for common electrochemical measurement. That is, a potentiostat which is used for common electrochemical measurement can be used as part of the hydrogel production apparatus without any special change. For this reason, in the example of FIG. 1, the potentiostat 50 includes an ammeter 53 like a potentiostat which is used for common electrochemical measurement.

The controller 85 applies a predetermined voltage between the working electrode 20 selected by operation (ON/OFF) performed on the switch 60 and the one counter electrode 30. The hydrogel production apparatus 800 can further have a configuration which is useful for production of a hydrogel (a detailed illustration thereof is omitted in FIG. 1). This useful configuration will be described later.

Figure 2:
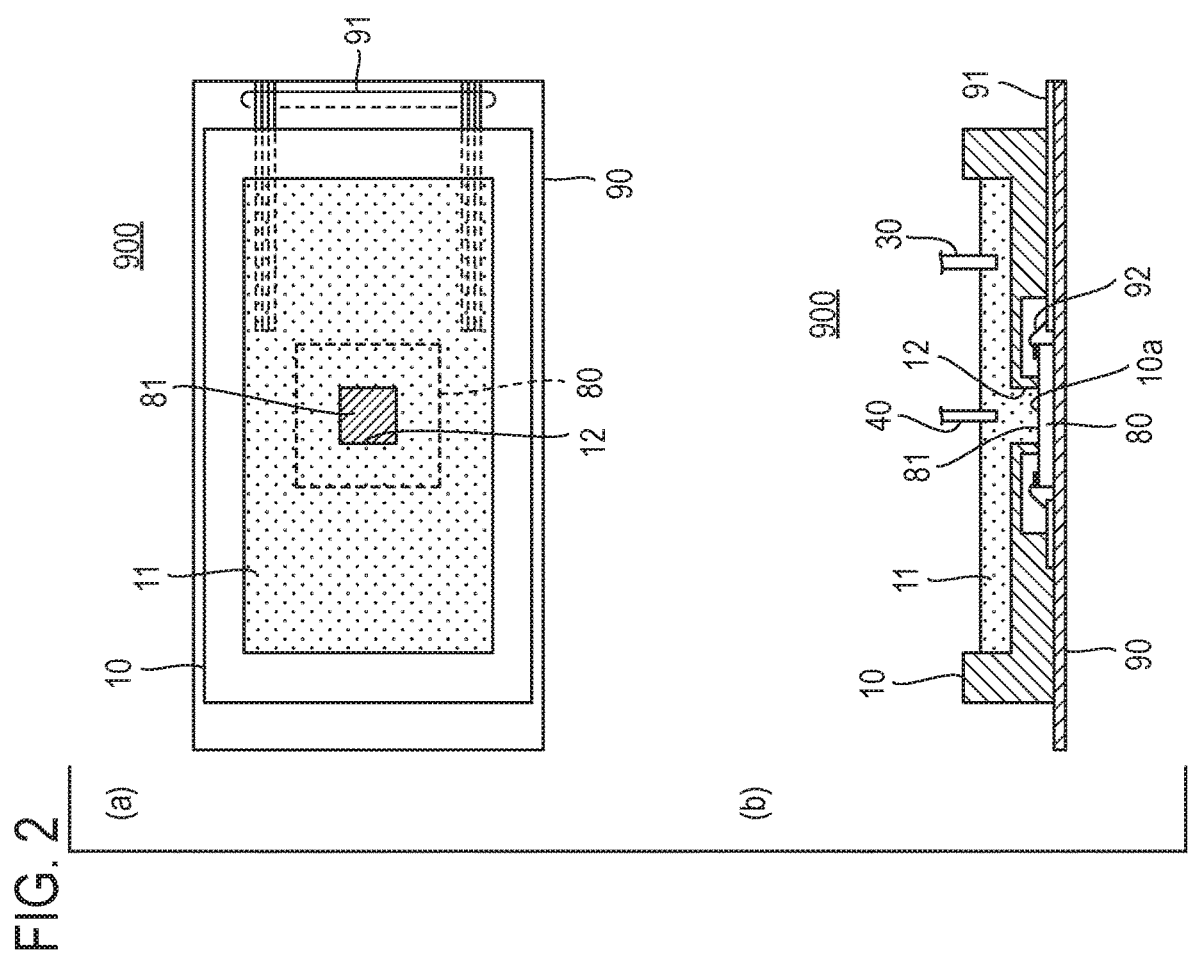
FIG. 2 is a diagram for explaining the configuration of a transducer of an embodiment: (a) a plan view; (b) a sectional view; (c) a diagram depicting the arrangement of cells of an LSI chip; and (d) a diagram depicting a working electrode provided in each cell.

Next, the transducer will be described. The transducer includes the hydrogel production apparatus and an integrated circuit. The bottom surface of the electrolytic tank is the front surface of the integrated circuit. The configuration of a transducer 900 will be described with reference to FIG. 2.

The transducer 900 has a configuration in which the electrolytic tank 10 covers an LSI chip 80. A hole 12 in the shape of a rectangle is formed in the center of the bottom of the electrolytic tank 10. The LSI chip 80 is disposed at the lower end of the hole 12 and closes the hole 12.

The LSI chip 80 and the electrolytic tank 10 are fixed on a substrate 90. A large number of wiring patterns 91 for connection with an external device (which is not depicted in the drawing) which performs control of the LSI chip 80 are formed on the substrate 90. In FIG. 2(b), a reference numeral 92 denotes bonding wires that connect the LSI chip 80 and the wiring patterns 91.

A shaping area 81 (a diagonally hatched portion in FIG. 2(a)) for producing a hydrogel with a pattern is set on the upper surface of the LSI chip 80. Specifically, the shaping area 81 is set in the position of the hole 12 of the electrolytic tank 10 and faces the electrolytic solution 11. In the position of the hole 12, the shaping area 81 is part of the bottom surface 10a of the electrolytic tank 10.

In this example, as depicted in FIG. 2(c), cells 82 are arranged in the shaping area 81 in the form of a two-dimensional grid array. One working electrode (a first electrode) 20 is formed in each cell 82 (see FIGS. 2(c) and (d)). In this example, 20×20=400 cells 82 are arranged with 250-μm pitches in the form of a two-dimensional grid array. That is, the LSI chip 80 has 400 working electrodes 20 arranged in the form of a two-dimensional grid array.

The LSI chip 80 has a function of applying a voltage between the counter electrode 30 and each working electrode 20, a switching function, and so forth. The one counter electrode 30 and the one reference electrode 40 are installed in the electrolytic solution 11. The reference electrode 40 is located immediately above the shaping area 81, and the counter electrode 30 is located apart from the reference electrode 40 (see FIG. 2(b)). The transducer 900 can further have a configuration which is useful for production of a hydrogel (a detailed illustration thereof is omitted in FIG. 2). This useful configuration will be described later.

Here, the principles of production of a hydrogel by an electrochemical method will be described.

Figure 3:
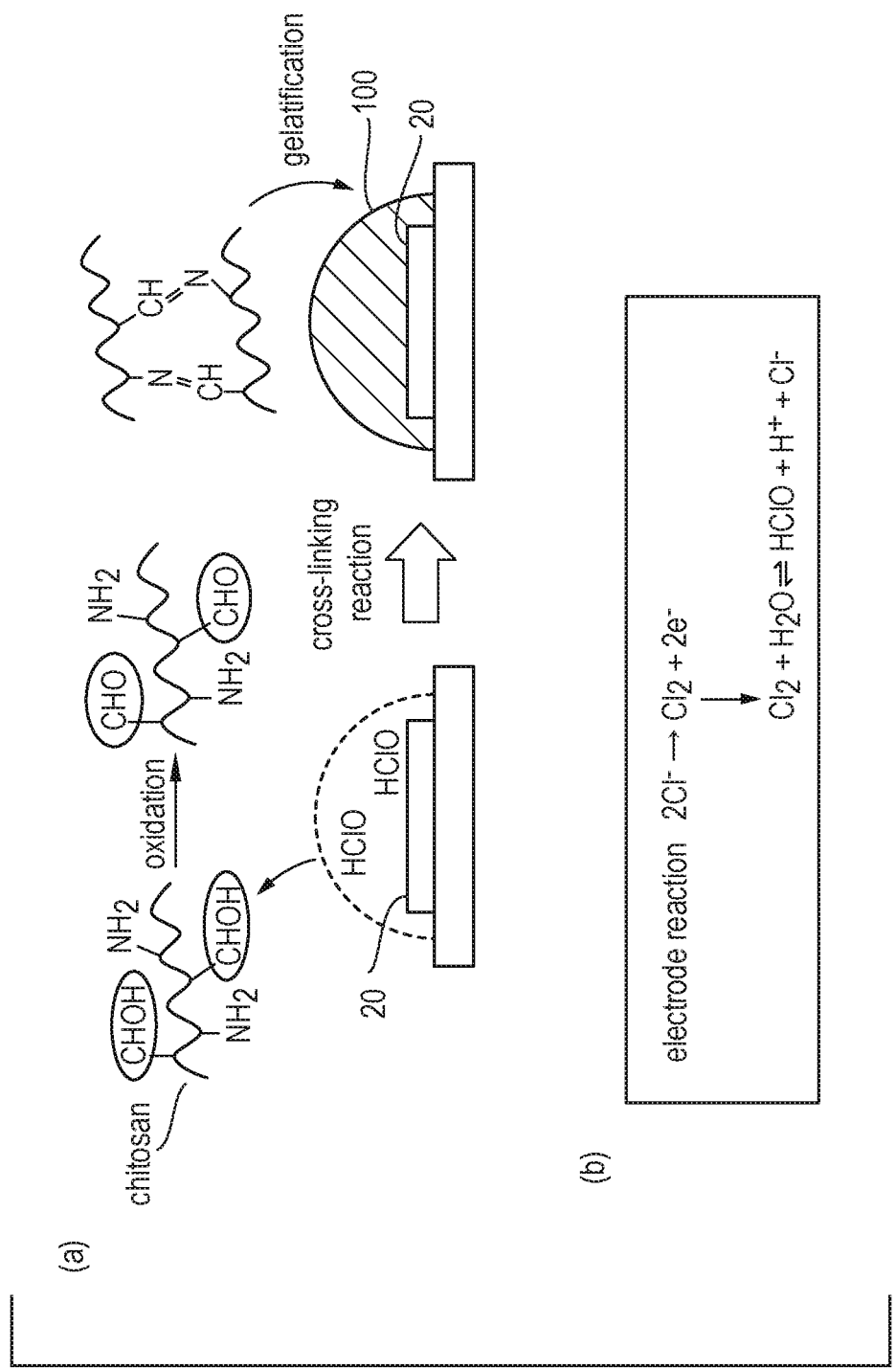
FIG. 3 is a diagram for explaining electrochemical hydrogel production.

A method of electrochemically producing a hydrogel is classified into three types.
1) Gelation of dispersoids caused by cross-linking
2) Cohesion of charged polymers caused by electrostatic interaction
3) Transformation of monomers into polymers by polymerization FIG. 3 depicts how a hydrogel is produced by a cross-linking reaction, with chitosan being taken up as an example. When a voltage is applied between the counter electrode (an electrode) 30 and the working electrode (an electrode) 20 in an aqueous solution in which chitosan and chlorine ions are present, hypochlorous acid (HClO) is generated by an electrode reaction (see FIG. 3(b)). Chitosan is oxidized by hypochlorous acid (see FIG. 3(a)). Then, a cross-linking reaction occurs between the chitosan molecules, and a hydrogel 100, which is insoluble in a solvent, is deposited on the working electrode 20.

The example is not limited to chitosan; for example, a hydrogel of gelatin or sodium alginate can also be produced based on a cross-linking reaction. Examples of specific conditions of aqueous solutions in cases where chitosan is used and gelatin is used are as follows.

chitosan: 1% (w/v) solution (0.15 M NaCl, adjusted by acetic acid so as to be pH 5.5)

gelatin: 10% (w/v) solution (4 M NaCl, 10 mM acetate buffer adjusted so as to be pH 5.6)

A method of producing a hydrogel according to the present invention includes a process of producing a hydrogel by any one of reactions: 1) cross-linking between dispersoids, 2) electrostatic interaction, and 3) polymerization, which are started by an electrode reaction. The method of producing a hydrogel uses electrolytic deposition of a hydrogel by which a hydrogel is generated by a reaction induced, in an electrolytic solution, by an electrode product electrochemically generated by electrodes installed in the electrolytic solution.

According to an embodiment of the present invention, in the hydrogel production apparatus 800 and the transducer 900, an electrolytic solution containing a precursor (i.e., dispersoids, charged polymers, monomers) of a hydrogel as a dissolved substance is housed in the electrolytic tank (a housing step) and, by applying a predetermined voltage between one or more selected working electrodes of the working electrodes arranged in the form of a two-dimensional array and the one counter electrode 30, a hydrogel with a two-dimensional pattern or a three-dimensional pattern corresponding to the arrangement of the selected working electrodes is produced (a production step).

A method of producing a hydrogel with a three-dimensional pattern includes a first step and a second step.

<First Step>

By applying a first voltage, which is a predetermined voltage, between all the working electrodes included in a first working electrode group and one counter electrode, a hydrogel with a first pattern, which is a two-dimensional pattern, is produced on the bottom surface of the electrolytic tank. The first working electrode group is made up of one or more selected working electrodes of the working electrodes 20.

<Second Step>

By applying a second voltage, which is a predetermined voltage, between all the working electrodes included in a second working electrode group and one counter electrode, a hydrogel with a second pattern, which is a two-dimensional pattern, is produced on the bottom surface of the electrolytic tank. Since the second pattern connects to the bottom surface of the first pattern, a hydrogel with a three-dimensional pattern as a whole is produced on the bottom surface of the electrolytic tank. The second working electrode group is made up of one or more selected working electrodes of the working electrodes 20. At least one working electrode included in the first working electrode group makes up the second working electrode group.

By performing the second step after the first step, a hydrogel with a three-dimensional pattern with a two-layer structure is produced. In the hydrogel with a three-dimensional pattern with a two-layer structure, the hydrogel with the second pattern directly connects to the bottom surface (a surface, of the two surfaces perpendicular to a Z direction, closer to the bottom surface of the electrolytic tank) of the hydrogel with the first pattern.

When all the working electrodes included in the first working electrode group are included in the second working electrode group, a three-dimensional pattern having a structure in which the first pattern is supported from below by the second pattern can be produced.

Figure 4:
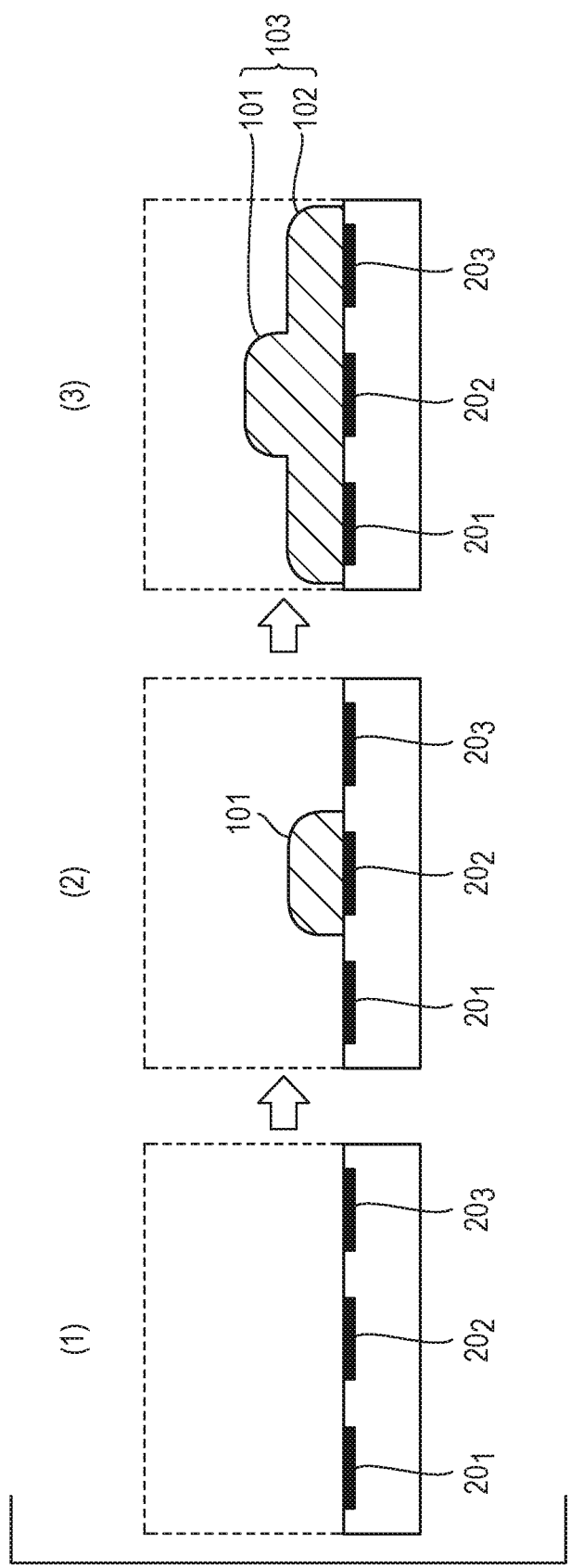
FIG. 4 is a diagram for explaining a method of electrochemically producing a hydrogel (an embodiment).

FIG. 4 is a schematic diagram explaining a process of producing a hydrogel having a structure in which the first pattern is supported from below by the second pattern. When a voltage is applied between the counter electrode 30 and a working electrode $20_2$, a hydrogel 101 is produced on the working electrode $20_2$ as depicted in FIG. 4(2). Next, when a voltage is applied between the counter electrode 30 and working electrodes $20_1$, $20_2$, and $20_3$, a hydrogel 102 is produced on the working electrodes $20_1$, $20_2$, and $20_3$ as depicted in FIG. 4(3). As a result, a hydrogel 103 with a three-dimensional pattern having a structure in which the hydrogel 101 with the first pattern is supported from below by the hydrogel 102 with the second pattern is produced.

Figure 5:
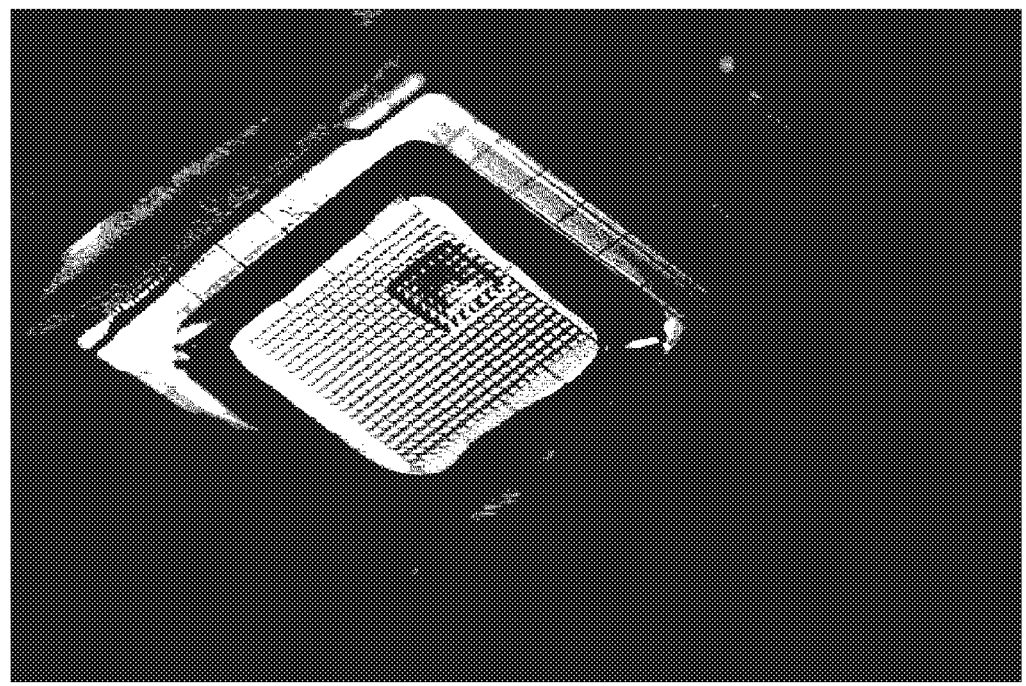
FIG. 5 is a photograph of a hydrogel actually produced by the method of electrochemically producing a hydrogel (an embodiment).

FIG. 5 is a photograph of the actually produced hydrogel with a three-dimensional pattern. This hydrogel was produced by applying a voltage between the counter electrode 30 and the selected working electrodes 20 in a chitosan 1% (w/v) aqueous solution with the above-described conditions by using the transducer 900 depicted in FIG. 2. Two voltage application modes (V1 mode, V2 mode) were started at the same time.

V1 mode: 0 V, 20 s→0.95 V, 10 s

V2 mode: 0.95 V, 30 s

Specifically, a voltage in V1 mode was applied between the counter electrode 30 and the working electrodes 20 of the diagonally hatched cells 82 (see FIG. 2(c)) and a voltage in V2 mode was applied between the counter electrode 30 and the working electrodes 20 of the cells 82 with a dot pattern (see FIG. 2(c)). In other words, a voltage of 0.95 V was applied only between the counter electrode 30 and the working electrodes 20 of the cells 82 with a dot pattern for first 20 seconds and, for subsequent 10 seconds, a voltage of 0.95 V was applied between the counter electrode 30 and the working electrodes 20 of the diagonally hatched cells 82 and between the counter electrode 30 and the cells 82 with a dot pattern.

It is understood from FIG. 5 that a hydrogel with a three-dimensional pattern was produced in accordance with the arrangement of the selected working electrodes 20 and the voltage application mode (V1 mode, V2 mode). In this experiment, the constituent materials of the working electrodes 20, the counter electrode 30, and the reference electrode 40 of the transducer 900 are as follows.

The working electrodes 20: Au

The counter electrode 30: Pt

The reference electrode 40: Ag/AgCl

When a hydrogel with a two-dimensional pattern is produced, the second step is unnecessary because a hydrogel with a two-dimensional pattern is produced only by the first step.

An embodiment is also admissible in which a step of discharging the electrolytic solution used in the first step from the electrolytic tank 10 and housing an electrolytic solution which is used in the second step in the electrolytic tank 10 is executed between the first step and the second step. In this case, preferably, the electrolytic solution which is used in the second step is different from the electrolytic solution used in the first step (at least one of the solvent and the dissolved substance of the electrolytic solution which is used in the second step is different from that of the electrolytic solution which is used in the first step). According to such an embodiment, it is possible to produce a hydrogel with a three-dimensional pattern with an alginate hydrogel on a chitosan hydrogel, for example.

Second Embodiment

A hydrogel with a three-dimensional pattern with a layered structure such as the above-mentioned two-layer structure can be satisfactorily obtained by using a Z stage. The Z stage is a device that has an adhesion surface parallel to the bottom surface of the electrolytic tank and can move the adhesion surface in the Z direction perpendicular to the bottom surface of the electrolytic tank.

A second embodiment of the hydrogel production apparatus includes the Z stage in addition to the configuration depicted in FIG. 1. A second embodiment of the transducer includes the Z stage in addition to the configuration depicted in FIG. 2. The Z stage included in the hydrogel production apparatus has a configuration in which the Z stage is independent of the hydrogel production apparatus or a configuration in which the Z stage is incorporated into the hydrogel production apparatus. In the hydrogel production apparatus, the adhesion surface of the Z stage is disposed parallel to the bottom surface 10a of the electrolytic tank 10. Likewise, the Z stage included in the transducer has a configuration in which the Z stage is independent of the transducer or a configuration in which the Z stage is incorporated into the transducer. In the transducer, the adhesion surface of the Z stage is disposed parallel to the shaping area 81.

The use of the Z stage makes it possible to produce a hydrogel with a desired three-dimensional pattern satisfactorily by the following procedure.

a) In the first step, in a state in which the adhesion surface of the Z stage is apart from the bottom surface of the electrolytic tank by a first distance in the electrolytic solution, a hydrogel with the first pattern, which is a two-dimensional pattern, is produced on the bottom surface of the electrolytic tank. The upper surface (a surface, of the two surfaces perpendicular to the Z direction, farther apart from the bottom surface) of the produced hydrogel adheres to the adhesion surface of the Z stage.

b) After the first step, the adhesion surface of the Z stage moves, with the hydrogel adhering to the adhesion surface of the Z stage, to a position apart from the bottom surface of the electrolytic tank by a predetermined distance, which is longer than the first distance, in the electrolytic solution. The lower surface (a surface, of the two surfaces perpendicular to the Z direction, closer to the bottom surface) of the hydrogel is separated from the bottom surface of the electrolytic tank and apart from the bottom surface of the electrolytic tank by a second distance (a separation step).

c) After the separation step, in the state in which the lower surface of the hydrogel with the first pattern is apart from the bottom surface of the electrolytic tank by the second distance, a hydrogel with the second pattern, which is a two-dimensional pattern, is produced on the bottom surface of the electrolytic tank. Since the second pattern connects to the bottom surface of the first pattern, a hydrogel with a three-dimensional pattern as a whole is produced on the bottom surface of the electrolytic tank.

A part, which is immersed in the electrolytic solution, of the Z stage is preferably made of glass, for example, from the viewpoint of preventing deterioration caused by an electrochemical reaction. Although glass is a material having an affinity for water, it is preferable to perform additional treatment on the adhesion surface of the Z stage to enhance an affinity for water. Examples of this treatment include the application of polyethylene glycol, for instance.

Figure 6:
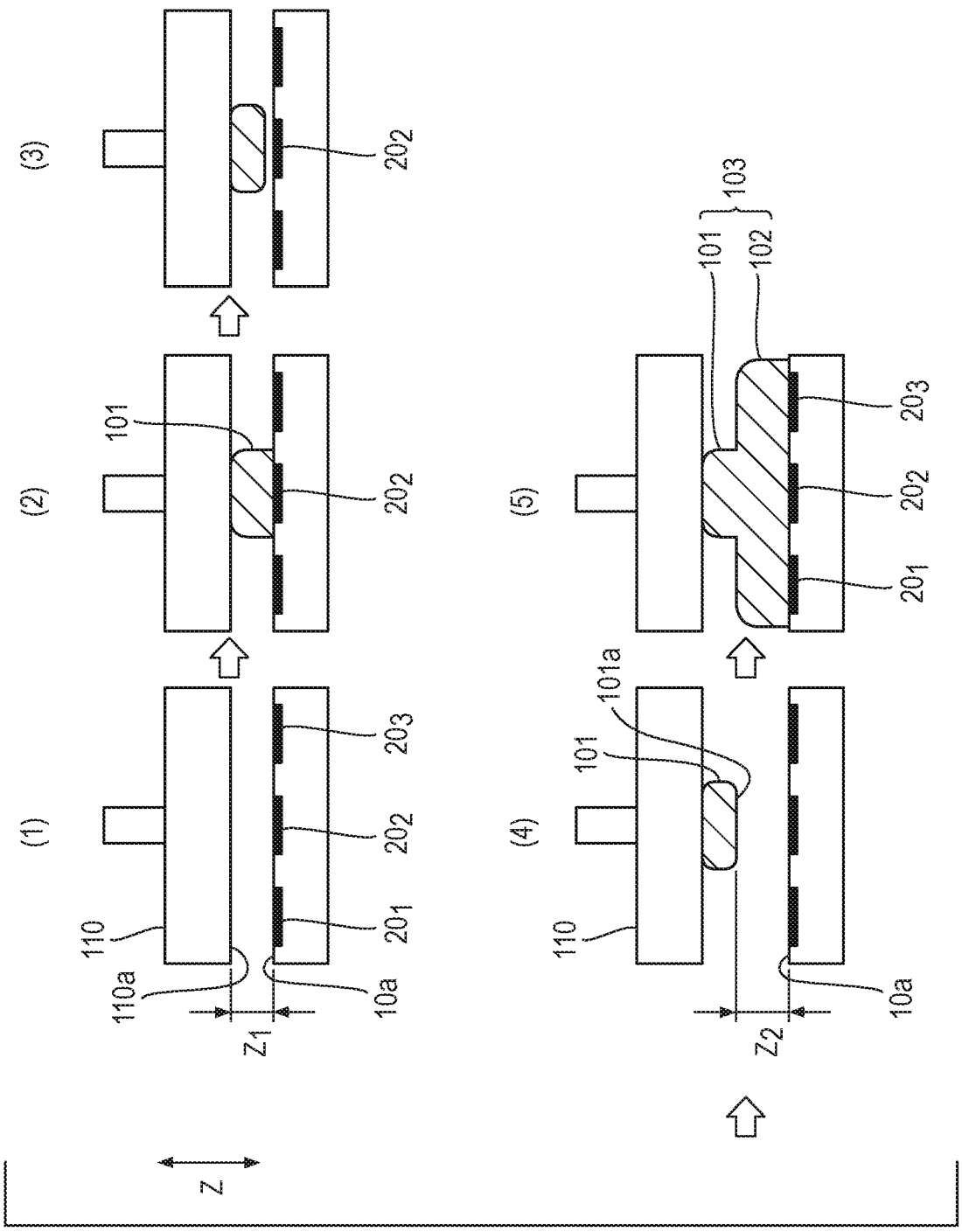
FIG. 6 is a diagram for explaining the method of electrochemically producing a hydrogel (an embodiment).

FIG. 6 is a schematic diagram depicting a process of producing the hydrogel depicted in FIG. 4 by using the Z stage.

An adhesion surface 110a of a Z stage 110 is apart from the bottom surface 10a of the electrolytic tank by a first distance Z in the electrolytic solution. By applying a voltage between the counter electrode 30 and the working electrode $20_2$ in this state, the hydrogel 101 with the first pattern is formed on the working electrode $20_2$. As depicted in FIG. 6(2), the upper surface of the hydrogel 101 adheres to the adhesion surface 110a. The separation step in which the hydrogel 101 is separated from the working electrode $20_2$ (see FIG. 6(3)) will be described later in detail.

As depicted in FIG. 6(4), the adhesion surface 110a of the Z stage 110 moves to a position apart from the bottom surface 10a of the electrolytic tank by a predetermined distance, which is longer than the first distance $Z_1$, in the electrolytic solution with the hydrogel 101 adhering to the adhesion surface 110a of the Z stage 110. A lower surface 101a of the hydrogel 101 is apart from the bottom surface 10a of the electrolytic tank by a second distance $Z_2$. By applying a voltage between the counter electrode 30 and the working electrodes $20_1$ to $20_3$ in this state, the hydrogel 102 with the second pattern is produced on the working electrodes $20_1$ to $20_3$ as depicted in FIG. 6(5). The hydrogel 103 with a three-dimensional pattern, which is made up of the hydrogel 101 and the hydrogel 102, is satisfactorily produced.

When all the working electrodes included in the second working electrode group are included in the first working electrode group in the process of producing a hydrogel by using the Z stage, a three-dimensional pattern having a structure in which the first pattern has the second pattern, which is smaller than the first pattern, hanging therefrom (in other words, when the bottom surface 10a of the electrolytic tank 10 or the shaping area 81 is viewed squarely, a structure in which: a) the whole of the second pattern is included in the first pattern; b) the area of the second pattern is smaller than the area of the first pattern; and c) the first pattern is on the second pattern) is satisfactorily produced. That is, a hydrogel with an inverted pyramid-shaped pattern is satisfactorily produced.

The following is an additional explanation of the hydrogel separation step (see FIG. 6(3)).

The separation step is performed in a state in which the hydrogel 101 with the first pattern is in contact with the working electrode $20_2$. In the separation step, a hydrogel separation voltage, which is different from the voltage used in the production of the hydrogel 101, is applied between the counter electrode 30 and the working electrode $20_2$. As a result of the application of the hydrogel separation voltage, a part of the hydrogel 101 in which the hydrogel 101 is in contact with the working electrode $20_2$ is dissolved, and the hydrogel 101 is separated from the working electrode $20_2$. The separation step allows the hydrogel 101 to move with the Z stage 110 while adhering to the adhesion surface 110a of the Z stage 110 (see FIG. 6(4)).

The separation step using the hydrogel separation voltage is useful when a sodium alginate solution, for instance, is used for production of a hydrogel. The reason is as follows: in the case of a sodium alginate solution, when a voltage which causes an oxidation reaction is applied between the counter electrode and the working electrode, an alginate hydrogel is deposited and, when a voltage which causes a reduction reaction is applied between the counter electrode and the working electrode, the alginate hydrogel is dissolved.

However, the separation step using the hydrogel separation voltage is not an indispensable step. Easy separation of the hydrogel from the working electrode is made possible by, for example, reducing the contact area between the hydrogel and the bottom surface 10a of the electrolytic tank. In this mode example, all the working electrodes arranged in the form of a two-dimensional array protrude from the bottom surface of the electrolytic tank. The side faces of the working electrodes are surrounded with insulators protruding from the bottom surface of the electrolytic tank.

FIGS. 7A(1)-(3) are schematic diagrams depicting an example of a method of producing the working electrodes and the insulators which protrude from the bottom surface of the electrolytic tank. As depicted in FIG. 7A(2), insulators 25 which form micro wells are produced on the working electrodes 20 by photolithography. Then, electrodes are produced by filling the insides of the micro wells with plating. As a result, as depicted in FIG. 7A(3), working electrodes 20a which protrude from the bottom surface 10a of the electrolytic tank and have the side faces surrounded with the insulators 25 are produced.

A hydrogel 104 produced by applying a voltage between the counter electrode 30 and the working electrodes 20a has a shape which does not make contact with the bottom surface 10a as depicted in FIG. 7B(2). Thus, the hydrogel 104 is easily separated from the working electrodes 20a at the time of movement of the Z stage 10 depicted in FIG. 7B(3).

Alternatively, easy separation of the hydrogel from the working electrode is made possible by, for example, the bottom surface 10a, which is rendered water-repellent, of the electrolytic tank. In this mode example, the bottom surface of the electrolytic tank other than the front surface of the working electrode is rendered water-repellent. Rendering the bottom surface water-repellent is, for example, coating the bottom surface with a thin film of fluorocarbon resin such as polytetrafluoroethylene (PTFE).

The separation step using the hydrogel separation voltage can also be applied to other embodiments.

Third Embodiment

Next, a method of producing a hydrogel with a three-dimensional pattern with a layered structure, in which different types of hydrogel are present in the same layer, will be described.

At least one of the above-described first step and second step includes a first sub-step and a second sub-step.

When the first step includes the first sub-step and the second sub-step, the first working electrode group includes a first sub-group and a second sub-group, the first voltage includes a first sub-voltage and a second sub-voltage, the first pattern includes a first sub-pattern and a second sub-pattern, and the second sub-group is made up of only the working electrode which does not belong to the first sub-group (in other words, the first sub-group and the second sub-group do not have a common working electrode).

When the second step includes the first sub-step and the second sub-step, the second working electrode group includes a first sub-group and a second sub-group, the second voltage includes a first sub-voltage and a second sub-voltage, the second pattern includes a first sub-pattern and a second sub-pattern, and the second sub-group is made up of only the working electrode which does not belong to the first sub-group (in other words, the first sub-group and the second sub-group do not have a common working electrode).

In this case, by applying the first sub-voltage between each working electrode included in the first sub-group and one counter electrode, a hydrogel with the first sub-pattern, which is a two-dimensional pattern, is produced, and, by applying the second sub-voltage between each working electrode included in the second sub-group and the one counter electrode, a hydrogel with the second sub-pattern, which is a two-dimensional pattern, is produced. Thus, different types of hydrogel are present in the same layer.

In the first sub-step and the second sub-step, for example, an electrode reaction in the first sub-step is an electrode reaction of oxidation and an electrode reaction in the second sub-step is an electrode reaction of reduction.

In the case of sodium alginate, a hydrogel is produced by an oxidation reaction. In the case of chitosan, in accordance with pH adjustment, a hydrogel is produced by an oxidation reaction under certain pH conditions and a hydrogel is produced by a reduction reaction under other pH conditions. When pH is set at conditions under which a chitosan hydrogel is produced by a reduction reaction, two types of hydrogel (a chitosan hydrogel and an alginate hydrogel) are produced in the first sub-step and the second sub-step.

FIG. 8 depicts an example in which each of the first step and the second step includes the first sub-step and the second sub-step. Specifically, FIG. 8 is a schematic diagram explaining production of a hydrogel in which, in a hydrogel with a multi-layer structure, each layer is formed of two types of hydrogel and two types of hydrogel are alternately located in the thickness direction (the Z direction) of the hydrogel. In FIG. 8, a reference numeral 105 denotes an alginate hydrogel and a reference numeral 106 denotes a chitosan hydrogel.

FIG. 8(2) depicts the first sub-step in the first step. The electrolytic tank 10 is filled with a sodium alginate solution. By applying the first sub-voltage ($V_{s1}$) between the first sub-group (the working electrode $20_2$) and the counter electrode 30, the alginate hydrogel 105 with the first sub-pattern is produced (the result of an oxidation reaction).

After the sodium alginate solution is removed from the electrolytic tank 10, the electrolytic tank 10 is filled with a chitosan solution.

FIG. 8(3) depicts the second sub-step in the first step. The electrolytic tank 10 is filled with the chitosan solution. By applying the second sub-voltage ($V_{s2}$) between the second sub-group (the working electrodes $20_1$ and $20_3$) and the counter electrode 30, the chitosan hydrogel 106 with the second sub-pattern is produced (the result of a reduction reaction).

Furthermore, though not depicted in the drawing, the first sub-step in the second step is executed. The electrolytic tank 10 is filled with the chitosan solution. By applying the first sub-voltage ($V_{s2}$) between the first sub-group (the working electrode $20_2$) and the counter electrode 30, the chitosan hydrogel 106 with the first sub-pattern is produced (the result of a reduction reaction). That is, the chitosan hydrogel 106 is produced under the alginate hydrogel 105 depicted in FIG. 8(3).

After the chitosan solution is removed from the electrolytic tank 10, the electrolytic tank 10 is filled with the sodium alginate solution.

Though not depicted in the drawing, the second sub-step in the second step is executed. The electrolytic tank 10 is filled with the sodium alginate solution. By applying the second sub-voltage ($V_{s1}$) between the second sub-group (the working electrodes $20_1$ and $20_3$) and the counter electrode 30, the alginate hydrogel 105 with the second sub-pattern is produced (the result of an oxidation reaction). That is, the alginate hydrogel 105 is produced under the chitosan hydrogel 106 depicted in FIG. 8(3).

By repeating the above-described procedure, a hydrogel 107 with a multi-layer structure (a four-layer structure in the example depicted in FIG. 8(4)) is produced.

In addition, an embodiment in which the above-described sub-steps are performed is permitted to have a modification including a sub-pattern removal step in which a selected hydrogel is removed. In the sub-pattern removal step, as one example, a hydrogel which is dissolved by predetermined treatment is produced in the second sub-step and, by performing the predetermined treatment after the first sub-step and the second sub-step, the hydrogel with the second sub-pattern is dissolved.

Specifically, for example, degradation of the alginate hydrogel by the addition of an alginate degrading enzyme is used. After the alginate hydrogel with the second sub-pattern is produced, the alginate degrading enzyme is diffused in the electrolytic solution. As a result, the second sub-pattern is selectively removed. The example is not limited to an enzyme; cross-linking scission by light irradiation, dissolution of gel by control of any one of pH and the temperature or both, and the like can also be used in the sub-pattern removal step.

When a hydrogel with a two-dimensional pattern is produced, as described earlier, only the first step is executed. In this case, a mode in which the first step includes the first sub-step and the second sub-step is also included in the embodiments of the present invention.

Fourth Embodiment

Next, a method of producing a hydrogel with a pattern formed of cells will be described. In this example, predetermined cells are distributed over a hydrogel which is a scaffold.

In the method of producing a hydrogel with a pattern formed of cells, a suspension containing a precursor of a hydrogel and predetermined cells is used as the electrolytic solution. By using this suspension, it is possible to produce a hydrogel, in which the predetermined cells are dispersed, on the bottom surface of the electrolytic tank.

The above-described method of producing a hydrogel is divided into the following four types.
a) A method including only the first step
b) A method including only the first step, which includes the first sub-step and the second sub-step
c) A method including the first step and the second step
d) A method including the first step and the second step, at least one of which includes the first sub-step and the second sub-step In the case of a), a suspension containing a precursor of a hydrogel and predetermined cells is used as the electrolytic solution which is used in the first step.

In the case of b), in at least one of the first sub-step and the second sub-step, a suspension containing a precursor of a hydrogel and one type of cell, for example, is used as the electrolytic solution. The electrolytic solution which is used in the first sub-step and the electrolytic solution which is used in the second sub-step may be different from each other (at least one of the solvent and the dissolved substance of the electrolytic solution which is used in the first sub-step and that of the electrolytic solution which is used in the second sub-step are different from each other). For instance, a suspension containing a precursor X of a hydrogel and one type of cell Y1 is used as the electrolytic solution which is used in the first sub-step and a suspension containing the precursor X of a hydrogel and one type of cell Y2 (Y1≠Y2) is used as the electrolytic solution which is used in the second sub-step.

In the case of c), in at least one of the first step and the second step, a suspension containing a precursor of a hydrogel and one type of cell, for example, is used as the electrolytic solution. By using this suspension, any one of a hydrogel with the cells dispersed therein and with the first pattern and a hydrogel with the cells dispersed therein and with the second pattern or both is produced.

In the case of c), the electrolytic solution which is used in the first step and the electrolytic solution which is used in the second step may be different from each other (at least one of the solvent and the dissolved substance of the electrolytic solution which is used in the first step and that of the electrolytic solution which is used in the second step are different from each other). For instance, a suspension containing a precursor X of a hydrogel and one type of cell Y1 is used as the electrolytic solution which is used in the first step and a suspension containing the precursor X of a hydrogel and one type of cell Y2 (Y1≠Y2) is used as the electrolytic solution which is used in the second step. As a result, a hydrogel with the cells Y1 dispersed therein and with the first pattern and a hydrogel with the cells Y2 dispersed therein and with the second pattern are produced.

As in the case of c), in the case of d), in at least one of the first sub-step and the second sub-step, a suspension containing a hydrogel precursor and one type of cell, for example, is used as the electrolytic solution.

Furthermore, as in the case of c), in the case of d), the electrolytic solution which is used in the first sub-step and the electrolytic solution which is used in the second sub-step may be different from each other (at least one of the solvent and the dissolved substance of the electrolytic solution which is used in the first sub-step and that of the electrolytic solution which is used in the second sub-step are different from each other).

Figure 9:
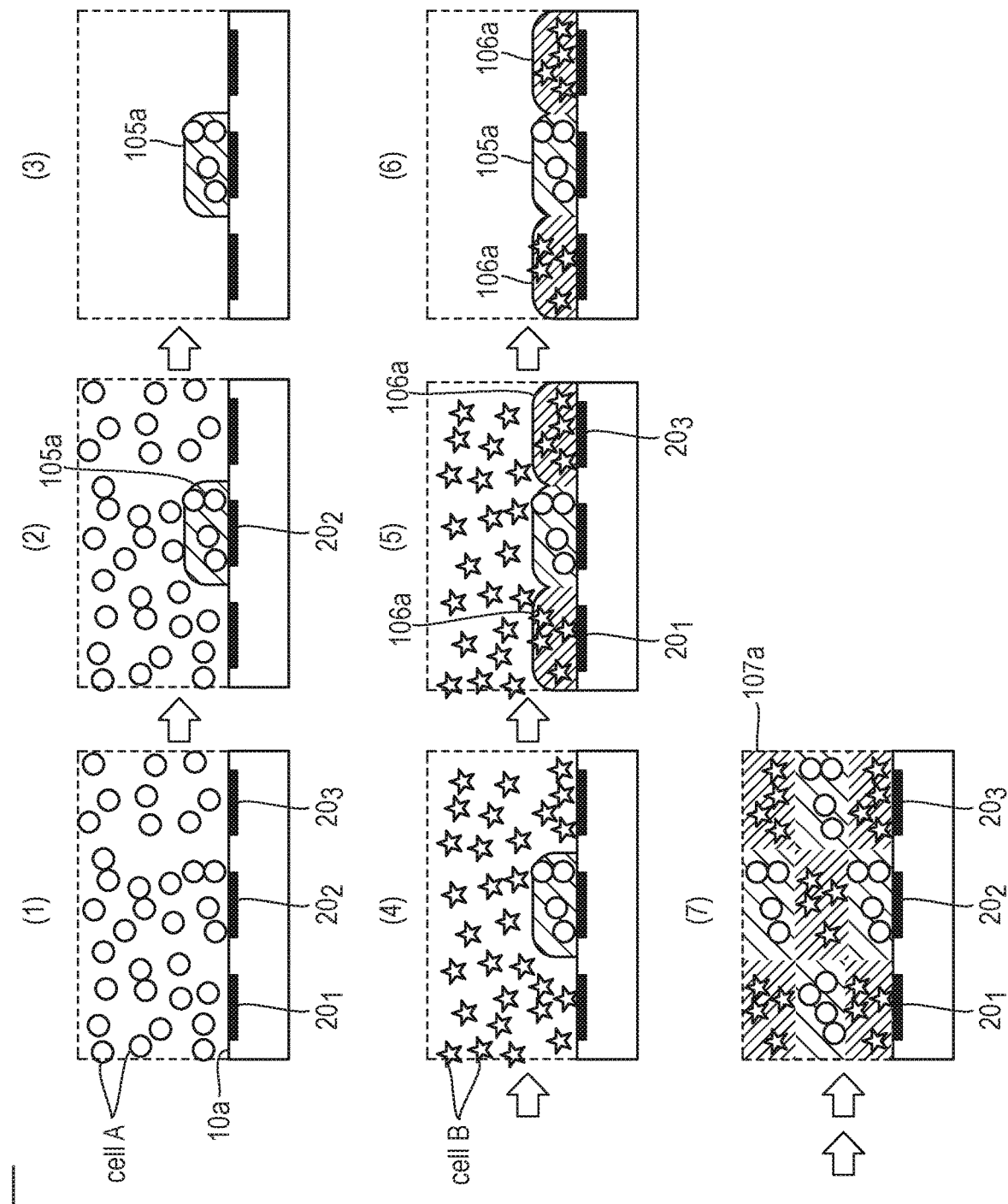
FIG. 9 is a diagram for explaining a method of producing a hydrogel with a pattern formed of cells (an embodiment).

FIG. 9 is a schematic diagram depicting a process of production of a multi-layer structure formed of an alginate hydrogel in which cells A are dispersed and a chitosan hydrogel in which cells B are dispersed.

The electrolytic tank 10 is filled with a suspension containing sodium alginate and the cells A (see FIG. 9(1)).

FIG. 9(2) depicts the first sub-step in the first step. By applying the first sub-voltage ($V_{s1}$) between the first sub-group (the working electrode $20_2$) and the counter electrode 30, an alginate hydrogel 105a with the first sub-pattern and with the cells A dispersed therein is produced (the result of an oxidation reaction).

After the suspension containing sodium alginate and the cells A is removed from the electrolytic tank 10 (see FIG. 9(3)), the electrolytic tank is filled with a suspension containing chitosan and the cells B (see FIG. 9(4)).

FIG. 9(5) depicts the second sub-step in the first step. The electrolytic tank 10 is filled with the suspension containing chitosan and the cells B. By applying the second sub-voltage ($V_{s2}$) between the second sub-group (the working electrodes $20_1$ and $20_3$) and the counter electrode 30, a chitosan hydrogel 106a with the second sub-pattern and with the cells B dispersed therein is produced (the result of a reduction reaction).

Furthermore, though not depicted in the drawing, the first sub-step in the second step is executed. The electrolytic tank 10 is filled with the suspension containing chitosan and the cells B. By applying the first sub-voltage ($V_{s2}$) between the first sub-group (the working electrode $20_2$) and the counter electrode 30, the chitosan hydrogel 106a with the first sub-pattern and with the cells B dispersed therein is produced (the result of a reduction reaction). That is, the chitosan hydrogel 106a is produced under the alginate hydrogel 105a depicted in FIG. 9(6).

After the suspension containing chitosan and the cells B is removed from the electrolytic tank 10, the electrolytic tank 10 is filled with the suspension containing sodium alginate and the cells A.

Though not depicted in the drawing, the second sub-step in the second step is executed. The electrolytic tank 10 is filled with the suspension containing sodium alginate and the cells A. By applying the second sub-voltage ($V_{s1}$) between the second sub-group (the working electrodes $20_1$ and $20_3$) and the counter electrode 30, the alginate hydrogel 105a with the second sub-pattern and with the cells A dispersed therein is produced (the result of an oxidation reaction). That is, the alginate hydrogel 105a is produced under the chitosan hydrogel 106a depicted in FIG. 9(6).

By repeating the above-described procedure, a hydrogel 107a with a multi-layer structure (a three-layer structure in the example depicted in FIG. 9(7)) is produced.

As described above, predetermined cells are dispersed in a hydrogel in a structural arrangement with a three-dimensional design. Thus, the present invention is useful for producing a desired cell culture structure.

An embodiment that produces a hydrogel in which predetermined cells are dispersed is permitted to have a modification including the above-described sub-pattern removal step. The above-described sub-pattern removal step is performed at the appropriate time in the process of producing a hydrogel in which predetermined cells are dispersed.

The type of cell which is used in the present invention is not limited to a particular type. For example, cells of any mammal, induced pluripotent stem (iPS) cells, embryonic stem (ES) cells, mesenchymal stem cells, hepatocytes, vascular endothelial cells, fibroblasts, and the like are used. For instance, in the case of vascular cells, by disposing vascular cells in a predetermined area of a hydrogel, it is possible to produce a blood vessel having a predetermined shape.

When a hydrogel with a pattern formed of cells is produced, it is preferable to use the cells efficiently. For this reason, for instance, it is preferable to perform a dielectrophoresis step in a state in which a suspension is housed in the electrolytic tank. The dielectrophoresis step is performed before a step of producing a hydrogel by applying a predetermined voltage between the selected working electrode and the counter electrode. In the dielectrophoresis step, an alternating voltage of a predetermined frequency is applied between the selected working electrode and the counter electrode and cells are densely distributed on the selected working electrode by dielectrophoresis. The directivity of phoresis (an affinity of cells to the density of electrical flux lines) is controlled by a frequency. The working electrode and the counter electrode in the dielectrophoresis step serve as a positive electrode and a negative electrode which alternate by an alternating voltage.

Figure 10:
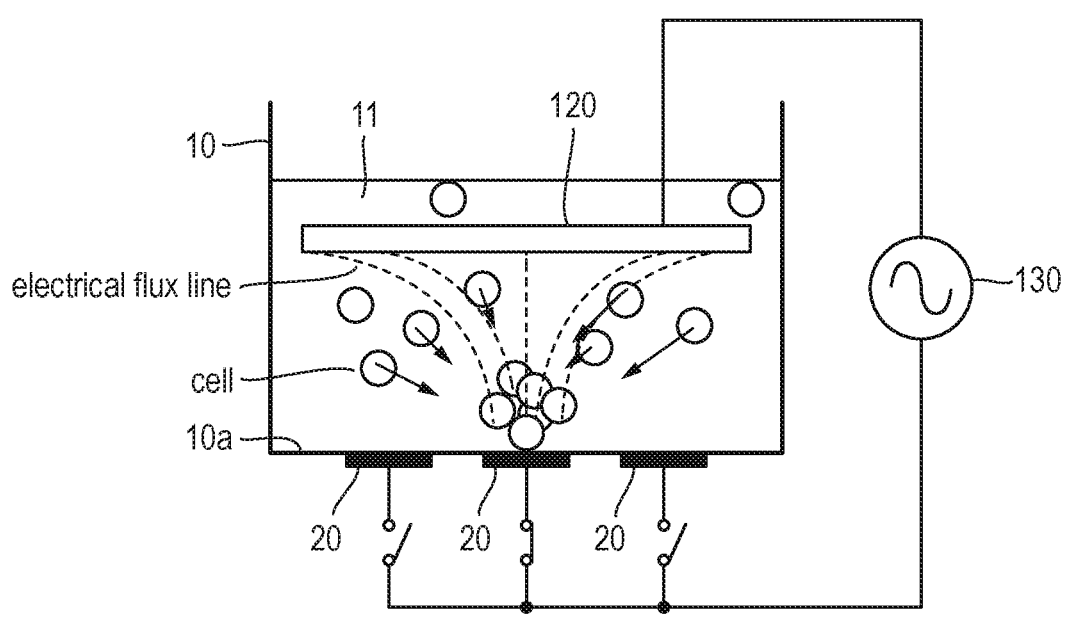
FIG. 10 is a diagram for explaining dielectrophoresis which is performed to concentrate cells on the working electrode.

FIG. 10 is a schematic diagram depicting how dielectrophoresis of cells is performed. In this example, an electrode 120 with an electrode plane parallel to the bottom surface 10a of the electrolytic tank 10 is used. The electrode plane of the electrode 120 faces a region in which the two-dimensional array of the working electrodes 20 is formed. In FIG. 10, a reference numeral 130 denotes an oscillator that applies an alternating voltage of a predetermined frequency between the working electrode 20 and the electrode 120. Moreover, a circle represents a cell and a dashed line represents an electrical flux line.

In the dielectrophoresis step, an electrode formed on the bottom surface 10a may be used in place of the electrode 120.

Figure 11:
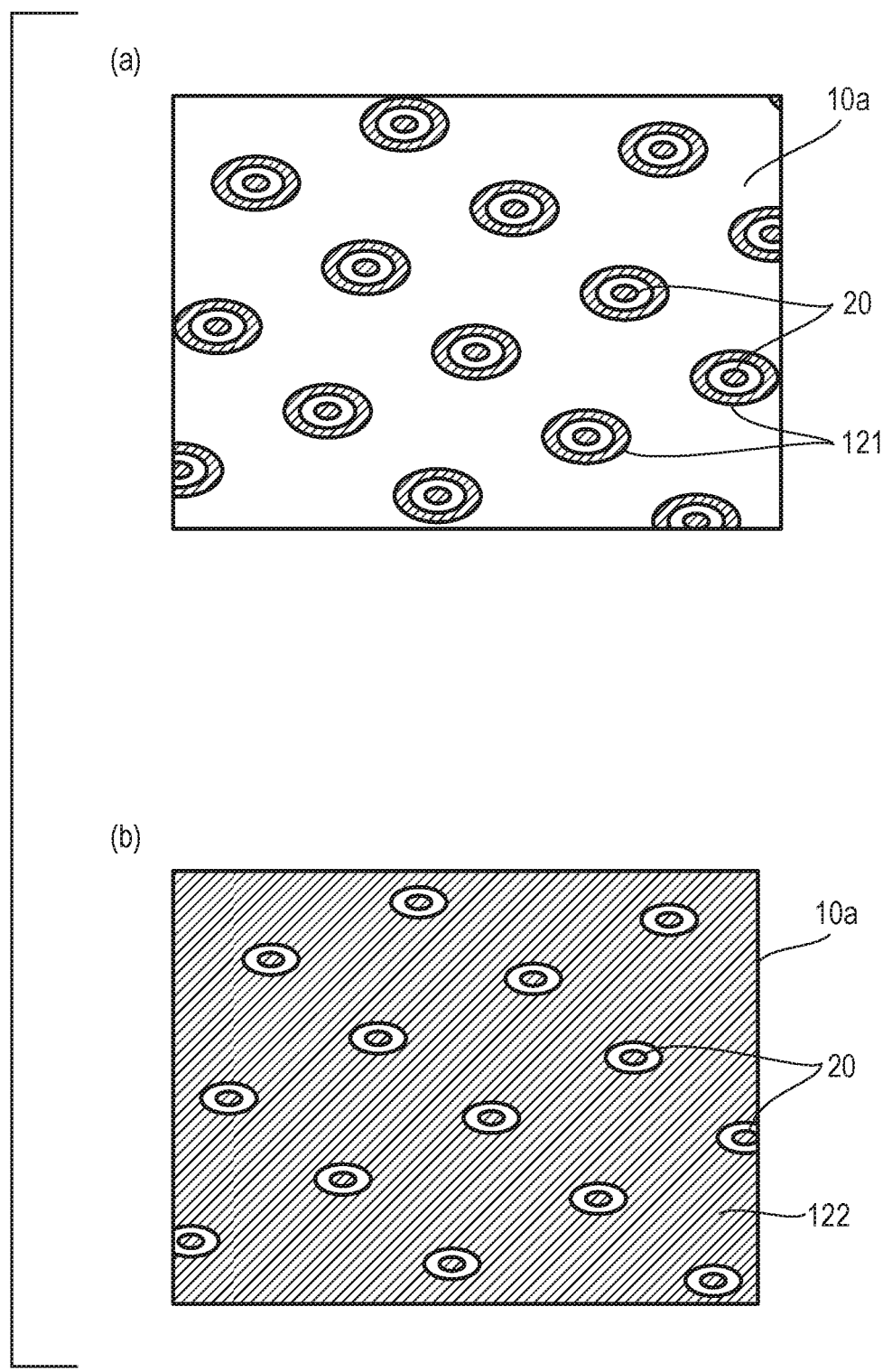
FIG. 11 is a diagram depicting an example of an electrode for dielectrophoresis: (a) an example of an annular electrode; and (b) an example of a solid electrode.

In a first example, for each working electrode 20, one electrode 121 for dielectrophoresis, which surrounds the working electrode 20, is formed on the bottom surface 10a (see FIG. 11(a)). Each electrode 121 has a ring-like shape. The electrode 121 and the working electrode 20 are not in contact with each other.

In a second example, one plate electrode 122 for dielectrophoresis is formed on the bottom surface 10a (see FIG. 11(b)). Holes corresponding to the positions of the working electrodes 20 are formed in the plate electrode 122. When the bottom surface 10a is viewed squarely, one working electrode 20 is located in one hole and the electrode 122 and the working electrode 20 are not in contact with each other.

When the dielectrophoresis step is performed, the hydrogel production apparatus 800 and the transducer 900 include the oscillator 130 in addition to the potentiostat 50. When the dielectrophoresis step is performed, the electrode 120 for dielectrophoresis, the electrode 121 for dielectrophoresis, or the electrode 122 for dielectrophoresis is a constituent element of the hydrogel production apparatus 800 or the transducer 900 or is a part which can be attached to the hydrogel production apparatus 800 or the transducer 900. When the Z stage 110 is not used in the production of a hydrogel, the electrode 120 does not interfere with the Z stage 110. Thus, in this case, the electrode 120 can be used as the counter electrode and the counter electrode 30 is unnecessary.

In the case of the transducer, as in the case of the working electrode 20 as the first electrode, the electrode 121 or the electrode 122 as a second electrode is formed in the shaping area 81 of the LSI chip 80. It is preferable to render a part of the shaping area 81 other than the front surface of the electrode water-repellent.

Since cells are negatively charged in general, in place of dielectrophoresis, electrophoresis can also be used to concentrate the cells densely on the selected working electrode. Electrophoresis is performed by applying a predetermined direct voltage between the selected working electrode and the counter electrode. In an electrophoresis step which is performed on the negatively charged cells, the working electrode serves as a positive electrode and the counter electrode serves as a negative electrode.

According to the present invention, it is possible to achieve a higher degree of flexibility in shaping, achieve greater versatility, and produce a hydrogel with a two-dimensional pattern or a three-dimensional pattern more efficiently than ever before. This makes it possible to produce a hydrogel of any shape accurately, easily, and quickly.

The present invention will be described as follows from a different perspective. It is to be noted that the following description is not contradictory to the disclosure described in the above-mentioned "MEANS TO SOLVE THE PROBLEMS" and it is possible to cross-reference the following description and the above-mentioned "MEANS TO SOLVE THE PROBLEMS" with each other.

Item 1

A method of electrochemically producing a hydrogel by using electrolytic deposition, the method including:

a step of housing an electrolytic solution containing a precursor of the hydrogel in an electrolytic tank, the electrolytic tank having a counter electrode therein and having a bottom surface with working electrodes arranged thereon; and a first step of producing the hydrogel with a first two-dimensional pattern on the bottom surface by applying a first voltage between the counter electrode and all the working electrodes included in a first working electrode group, the first working electrode group consisting of one or more ones selected from among the working electrodes.

Item 2

The electrochemical production method described in Item 1, further including a second step that is executed after the first step, wherein the second step includes producing on the bottom surface, by applying a second voltage between the counter electrode and all the working electrodes included in a second working electrode group, the hydrogel with a three-dimensional pattern in which a second two-dimensional pattern connects to a bottom surface of the first two-dimensional pattern, wherein the second working electrode group consists of one or more ones selected from among the working electrodes, and wherein one or more ones included in the first working electrode group are included in the second working electrode group.

Item 3

The electrochemical production method described in Item 2, including, between the first step and the second step, a step of discharging the electrolytic solution used in the first step from the electrolytic tank and housing, in the electrolytic tank, the electrolytic solution which is to be used in the second step, wherein the electrolytic solution used in the second step is different from the electrolytic solution used in the first step.

Item 4

The electrochemical production method described in Item 2 or 3, wherein either or both of the first step and the second step include a first sub-step and a second sub-step, wherein, when the first step includes the first sub-step and the second sub-step, the first working electrode group includes a first sub-group and a second sub-group, the first voltage includes a first sub-voltage and a second sub-voltage, the first pattern includes a first sub-pattern and a second sub-pattern, and the first sub-group and the second sub-group do not have a common working electrode, wherein, when the second step includes the first sub-step and the second sub-step, the second working electrode group includes a first sub-group and a second sub-group, the second voltage includes a first sub-voltage and a second sub-voltage, the second pattern includes a first sub-pattern and a second sub-pattern, and the first sub-group and the second sub-group do not have a common working electrode, wherein, by applying the first sub-voltage between the counter electrode and all the working electrodes included in the first sub-group, the hydrogel with the first sub-pattern is produced on the bottom surface, and wherein, by applying the second sub-voltage between the counter electrode and all the working electrodes included in the second sub-group, the hydrogel with the second sub-pattern is produced on the bottom surface.

Item 5

The electrochemical production method described in Item 4, including, between the first sub-step and the second sub-step, a step of discharging the electrolytic solution used in the first sub-step from the electrolytic tank and housing, in the electrolytic tank, the electrolytic solution which is to be used in the second sub-step, wherein the electrolytic solution used in the second sub-step is different from the electrolytic solution used in the first sub-step.

Item 6

The electrochemical production method described in Item 4 or 5, further including a sub-pattern removal step that is executed after the first sub-step and the second sub-step, wherein, in the first sub-step or the second sub-step, the hydrogel which is dissolved by predetermined treatment is produced, and wherein, in the sub-pattern removal step, the hydrogel with the first sub-pattern or the second sub-pattern is dissolved by performing the predetermined treatment.

Item 7

The electrochemical production method described in any one of Items 2 to 6, further including a separation step that is performed after the first step and before the second step, wherein the first step and the second step are performed by using a Z stage that has an adhesion surface parallel to the bottom surface of the electrolytic tank and moves the adhesion surface in a direction perpendicular to the bottom surface of the electrolytic tank, wherein in the first step, the hydrogel with the first two-dimensional pattern is produced between the adhesion surface, which is located apart from the bottom surface of the electrolytic tank by a first distance in the electrolytic solution, and the bottom surface of the electrolytic tank and is in contact with the adhesion surface, wherein in the separation step, in a process whereby the adhesion surface is moved in the electrolytic solution by the Z stage to a position apart from the bottom surface of the electrolytic tank by a predetermined distance, which is greater than the first distance, the hydrogel with the first two-dimensional pattern is separated from the bottom surface of the electrolytic tank while adhering to the adhesion surface, and wherein in the second step, the hydrogel with the three-dimensional pattern is produced between the adhesion surface and the bottom surface of the electrolytic tank and the second two-dimensional pattern is in contact with a bottom surface of the first two-dimensional pattern.

Item 8

The electrochemical production method described in Item 7, wherein the adhesion surface has an affinity for water.

Item 9

The electrochemical production method described in any one of Items 2 to 8, wherein the number of working electrodes included in the second working electrode group is greater than the number of working electrodes included in the first working electrode group, and wherein all the working electrodes included in the first working electrode group are included in the second working electrode group.

Item 10

The electrochemical production method described in Item 7 or 8, wherein the number of working electrodes included in the first working electrode group is greater than the number of working electrodes included in the second working electrode group, and wherein all the working electrodes included in the second working electrode group are included in the first working electrode group.

Item 11

The electrochemical production method described in any one of Items 1 to 10, wherein each of the working electrodes protrudes from the bottom surface, and wherein side faces of each of the working electrodes are surrounded with insulators protruding from the bottom surface of the electrolytic tank.

Item 12

The electrochemical production method described in any one of Items 1 to 11, wherein the bottom surface of the electrolytic tank other than front surfaces of the working electrodes is water-repellent.

Item 13

The electrochemical production method described in any one of Items 1 to 12, further including a step of dissolving, by applying a voltage, which is different from the first voltage, between the counter electrode and all the working electrodes included in the first working electrode group in a state in which the hydrogel with the first two-dimensional pattern is in contact with a working electrode included in the first working electrode group, a part of the hydrogel at which the hydrogel is in contact with the working electrode included in the first working electrode group.

Item 14

A method of producing a hydrogel with a pattern formed of cells, including a step of using an electrochemical production method that is the electrochemical production method described in any one of Items 1 to 13 and uses, as an electrolytic solution, a suspension containing a precursor of the hydrogel and the cells.

Item 15

The production method described in Item 14, further including a step of concentrating the cells on the first working electrode group by dielectrophoresis or electrophoresis before the first step or a step of concentrating the cells on the second working electrode group by dielectrophoresis or electrophoresis before the second step.

Item 16

A hydrogel production apparatus for producing a hydrogel by using electrolytic deposition, including:

an electrolytic tank with a counter electrode set therein, the electrolytic tank having a bottom surface with working electrodes arranged thereon;

a controller applying a voltage between the counter electrode and one or more ones selected from among the working electrodes; and a Z stage having an adhesion surface for the hydrogel's adhesion and moving the adhesion surface in a direction perpendicular to the bottom surface of the electrolytic tank while keeping the adhesion surface parallel to the bottom surface of the electrolytic tank.

Item 17

The hydrogel production apparatus described in Item 16, wherein the adhesion surface has an affinity for water.

Item 18

The hydrogel production apparatus described in Item 16 or 17, wherein each of the working electrodes protrudes from the bottom surface, and wherein side faces of the working electrodes are surrounded with insulators protruding from the bottom surface of the electrolytic tank.

Item 18

A hydrogel production apparatus for producing a hydrogel by using electrolytic deposition, including:

an electrolytic tank with a counter electrode set therein, the electrolytic tank having a bottom surface with working electrodes arranged thereon; and a controller applying a voltage between the counter electrode and one or more ones selected from among the working electrodes, each of the working electrodes protruding from the bottom surface, and side faces of the working electrodes being surrounded with insulators protruding from the bottom surface of the electrolytic tank.

Item 19

The hydrogel production apparatus described in any one of Items 16 to 18, wherein the bottom surface of the electrolytic tank other than front surfaces of the working electrodes is water-repellent.

Item 20

The hydrogel production apparatus described in any one of Items 16 to 19, further including:

an electrode for phoresis; and an oscillator that applies an alternating voltage of a predetermined frequency between the electrode for phoresis and one or more ones selected from among the working electrodes.

Item 21

A transducer including:

the hydrogel production apparatus described in any one of Items 16 to 20; and an integrated circuit, the bottom surface of the electrolytic tank being a front surface of the integrated circuit.

INDUSTRIAL APPLICABILITY

The technique of producing a hydrogel according to the present invention is useful in, for example, assessment of drugs as an alternative to animal testing, production of operation practice equipment, production of medical supplies, and so forth.

What is claimed is:

1. A method of electrochemically producing a hydrogel by using electrolytic deposition of the hydrogel, by which the hydrogel is formed by a reaction which is induced in an electrolytic solution by an electrode product electrochemically generated by electrodes installed in the electrolytic solution, the method comprising:

a preparing step which comprises providing an apparatus including an electrolytic tank and an electrolytic solution housed therein, the electrolytic tank having a two-dimensional array of working electrodes provided on a bottom surface thereof and a counter electrode installed in the electrolytic solution, the electrolytic solution containing a dissolved substance which causes electrolytic deposition of the hydrogel;

a first step which comprises forming a first layer hydrogel on the bottom surface of the electrolytic tank by applying a first voltage to a first working electrode group, the first layer hydrogel having a two-dimensionally defined first pattern, the first working electrode group being one or more selected working electrodes of the two-dimensional array of working electrodes, the first pattern corresponding to an arrangement of the first working electrode group; and a second step which comprises forming a second layer hydrogel on the bottom surface of the electrolytic tank by applying a second voltage to a second working electrode group, such that the second layer hydrogel directly connects to a bottom surface of the first layer hydrogel and supports the first layer hydrogel from below, the second layer hydrogel having a two-dimensionally defined second pattern the second working electrode group being one or more further selected working electrodes of the two-dimensional array of working electrodes, the second pattern corresponding to an arrangement of the second working electrode group, whereby the hydrogel having a three-dimensionally defined pattern including at least two layers comprising the first layer hydrogel and the second layer hydrogel is formed.

2. The method of electrochemically producing a hydrogel according to claim 1, wherein one of the first step and the second step includes a first sub-step and a second sub-step, a corresponding one of the first working electrode group and the second working electrode group includes a first working electrode sub-group and a second working electrode sub-group, a corresponding one of the first voltage and the second voltage includes a first sub-voltage and a second sub-voltage, and a corresponding one of the first pattern and the second pattern incudes a first sub-pattern and a second sub-pattern, the second working electrode sub-group consists of only working electrodes which do not belong to the first working electrode sub-group, and a hydrogel with the first sub-pattern is formed by applying the first sub-voltage to the first working electrode sub-group and a hydrogel with the second sub-pattern is formed by applying the second sub-voltage to the second working electrode sub-group.

3. The method of electrochemically producing a hydrogel according to claim 2, wherein in the second sub-step, a hydrogel which dissolves under a predetermined condition is formed as the hydrogel with the second sub-pattern, and the method further includes, after at least both of the first sub-step and the second sub-step, a sub-pattern removal step of selectively removing the hydrogel with the second sub-pattern by dissolving the hydrogel with the second sub-pattern by providing the hydrogel with the second sub-pattern with the predetermined condition.

4. The method of electrochemically producing a hydrogel according to claim 1, wherein the preparing step further comprises providing a Z stage that has an adhesion surface facing parallel the bottom surface of the electrolytic tank, the Z stage being displaceable in a Z direction perpendicular to the bottom surface of the electrolytic tank, the first step is performed in a state in which the Z stage is located at a first position in the Z direction in which the adhesion surface is apart from the bottom surface of the electrolytic tank by a first distance, so that an upper surface of the first layer hydrogel formed in the first step adheres to the adhesion surface of the Z stage, the upper surface being one of two surfaces perpendicular to the Z direction of the first layer hydrogel which is farther from the bottom surface of the electrolytic tank than an other of the two surfaces, the method further comprises a separation step performed between the first step and the second step, the separation step comprising separating the first layer hydrogel from the bottom surface of the electrolytic tank by displacing the Z stage from the first position into a second position in the Z direction in which a lower surface of the first layer hydrogel is located apart from the bottom surface of the electrolytic tank by a second distance, the lower surface being said an other of the two surfaces, wherein the upper surface of the first layer hydrogel is kept adhered to the adhesion surface of the Z stage during the separation step, and the second step is performed in a state in which the Z stage is located at the second position so that an upper surface of the second layer hydrogel formed in the second step connects to the lower surface of the first layer hydrogel.

5. The method of electrochemically producing a hydrogel according to claim 4, wherein the adhesion surface is subjected to treatment that makes the adhesion surface have an affinity for water.

6. The method of electrochemically producing a hydrogel according to claim 4, wherein all of the second working electrode groups are included in the first working electrode group, whereby the second layer hydrogel, which is smaller than the first layer hydrogel, hangs from the first layer hydrogel and is thereby supported from above.

7. The method of electrochemically producing a hydrogel according to claim 1, wherein all of the first working electrode groups are included in the second working electrode group, whereby the first layer hydrogel as a whole is supported from below by the hydrogel with the second pattern.

8. The method of electrochemically producing a hydrogel according to claim 1, wherein a working electrode included in the two-dimensional array of working electrodes protrudes from the bottom surface of the electrolytic tank and a side face of the protruding working electrode is surrounded with an insulating layer formed so as to protrude from the bottom surface along with the protruding working electrode.

9. The method of electrochemically producing a hydrogel according to claim 1, wherein a part of the bottom surface other than front surfaces of the working electrodes is made water-repellent.

10. The method of electrochemically producing a hydrogel according to claim 1, wherein at least one of the first step and the second step further comprises facilitating of separation of corresponding one of the first layer hydrogel and the layer hydrogel after forming thereof from corresponding one of the first working electrode group and the second working electrode group applying a hydrogel separating voltage to the corresponding working electrode group when the corresponding layer hydrogel is in contact therewith to dissolve a part of the corresponding layer hydrogel that contacts the corresponding working electrode group, the hydrogel separating voltage being different than corresponding one of the first voltage and the second voltage.

11. A method of producing a hydrogel patterned with cells, which is obtained by distributing prescribed cells over a hydrogel scaffold, wherein by performing the method of electrochemically producing a hydrogel according to claim 1 by using a suspension as the electrolytic solution containing the dissolved substance which causes electrolytic deposition of the hydrogel, the suspension further containing the prescribed cells, the hydrogel having distributed therein the prescribed cells is formed on the bottom surface of the electrolytic tank.

12. The method of producing a hydrogel patterned with cells according to claim 11, further comprising, before one of the first step and the second step, a dielectrophoresis step of densely distributing the prescribed cells above corresponding one of the first working electrode group and the second working electrode group by dielectrophoresis, by applying an alternating voltage of a predetermined frequency to the corresponding one of the first working electrode group and the second working electrode group.

13. The method of producing a hydrogel patterned with cells according to claim 12, wherein
in the dielectrophoresis step, an electrode with an electrode plane facing, parallel to the bottom surface, a region of the bottom surface in which the two-dimensional array of the working electrodes is provided is used.

14. The method of producing a hydrogel patterned with cells according to claim 12, wherein
in the dielectrophoresis step, an electrode which is provided on the bottom surface so as to be located around each of the two-dimensional array of the working electrodes is used.

15. The method of producing a hydrogel patterned with cells according to claim 11, further comprising,
before one of the first step and the second step, an electrophoresis step of densely distributing the prescribed cells above corresponding one of the first working electrode group and the second working electrode group by electrophoresis, by applying a predetermined direct voltage to the corresponding one of the first working electrode group and the second working electrode group.

16. A method of producing a hydrogel patterned with cells, which is obtained by distributing prescribed cells over a hydrogel scaffold, wherein
the prescribed cells include one or more types of cells, and
the method includes a step of performing the method of electrochemically producing a hydrogel according to claim 1, wherein one of the first step and the second step is performed by using a suspension as the electrolytic solution concerned, the suspension containing one type of cells included by the one or more types of cells along with the dissolved substance which causes electrolytic deposition of the hydrogel concerned.

17. The method of producing a hydrogel patterned with cells according to claim 16, wherein
the prescribed cells include at least two types of cells, and
an other of the first step and the second step is performed by using an other suspension as the electrolytic solution concerned, the other suspension containing an other type of cells included by the at least two types of cells, the other type of cells being different from the one type of cells, along with the dissolved substance which causes electrolytic deposition of the hydrogel concerned.

18. A method of producing a hydrogel patterned with cells, which is obtained by distributing prescribed cells over a hydrogel scaffold, wherein
the prescribed cells include one or more types of cells, and
the method includes a step of performing the method of electrochemically producing a hydrogel according to claim 2, wherein one of the first sub-step and the second sub-step is performed by using a suspension as the electrolytic solution concerned, the suspension containing one type of cells included by the one or more types of cells along with the dissolved substance which causes electrolytic deposition of the hydrogel concerned.

19. The method of producing a hydrogel patterned with cells according to claim 18, wherein
the prescribed cells include at least two types of cells, and
an other of the first sub-step and the second sub-step is performed by using an other suspension as the electrolytic solution concerned, the other suspension containing an other type of cells included by the at least two types of cells, the other type of cells being different from the one type of cells, along with the dissolved substance which causes electrolytic deposition of the hydrogel concerned.

* * * * *